US012599616B2

(12) United States Patent
Sharma et al.

(10) Patent No.: US 12,599,616 B2
(45) Date of Patent: Apr. 14, 2026

(54) SUBTITUTED SULFONYLUREA AND SULFOXIMINEUREA DERIVATIVES

(71) Applicant: Zydus Lifesciences Limited, Ahmedabad (IN)

(72) Inventors: Rajiv Sharma, Ahmedabad (IN); Sameer Agarwal, Ahmedabad (IN)

(73) Assignee: ZYDUS LIFESCIENCES LIMITED, Gujarat (IN)

( * ) Notice: Subject to any disclaimer, the term of this patent is extended or adjusted under 35 U.S.C. 154(b) by 795 days.

(21) Appl. No.: 17/800,261

(22) PCT Filed: Feb. 26, 2021

(86) PCT No.: PCT/IB2021/051596

§ 371 (c)(1),
(2) Date: Aug. 17, 2022

(87) PCT Pub. No.: WO2021/171230

PCT Pub. Date: Sep. 2, 2021

(65) Prior Publication Data

US 2023/0096220 A1 Mar. 30, 2023

(30) Foreign Application Priority Data

Feb. 28, 2020 (IN) ............................ 202021008578

(51) Int. Cl.

| | |
|---|---|
| ***A61K 31/64*** | (2006.01) |
| ***A61K 31/545*** | (2006.01) |
| ***A61K 38/20*** | (2006.01) |
| ***A61K 38/21*** | (2006.01) |
| ***A61K 45/06*** | (2006.01) |
| ***A61P 29/00*** | (2006.01) |
| ***C07C 311/55*** | (2006.01) |
| ***C07C 381/10*** | (2006.01) |
| ***C07D 211/58*** | (2006.01) |
| ***C07D 295/084*** | (2006.01) |
| ***C07D 295/088*** | (2006.01) |
| ***C07D 295/13*** | (2006.01) |
| ***C07D 309/14*** | (2006.01) |
| ***C07D 335/02*** | (2006.01) |

(52) U.S. Cl.

CPC ............ *A61K 31/64* (2013.01); *A61K 31/545* (2013.01); *A61K 38/20* (2013.01); *A61K 38/21* (2013.01); *A61K 45/06* (2013.01); *C07C 311/55* (2013.01); *C07C 381/10* (2013.01); *C07D 211/58* (2013.01); *C07D 295/084* (2013.01); *C07D 295/13* (2013.01); *C07D 309/14* (2013.01); *C07D 335/02* (2013.01); *C07C 2601/02* (2017.05); *C07C 2601/04* (2017.05); *C07C 2601/08* (2017.05); *C07C 2601/14* (2017.05); *C07C 2603/10* (2017.05)

(58) Field of Classification Search

CPC ...... A61K 31/64; A61K 31/545; A61K 38/20; A61K 38/21; A61K 45/06; C07C 311/55; C07C 381/10; C07C 2601/02; C07C 2601/04; C07C 2601/08; C07C 2601/14; C07C 2603/10; C07D 211/58; C07D 295/084; C07D 295/13; C07D 309/14; C07D 335/02; C07D 295/088; A61P 29/00

See application file for complete search history.

(56) References Cited

U.S. PATENT DOCUMENTS

2025/0041267 A1 * 2/2025 Agarwal ................ A61P 31/18

FOREIGN PATENT DOCUMENTS

| | | | |
|---|---|---|---|
| WO | 2017140778 | A1 | 8/2017 |
| WO | 2018225018 | A1 | 12/2018 |
| WO | 2019068772 | A1 | 4/2019 |
| WO | 2019043610 | A1 | 7/2019 |

* cited by examiner

*Primary Examiner* — Kamal A Saeed
*Assistant Examiner* — Sagar Patel
(74) *Attorney, Agent, or Firm* — RENNER, KENNER, GREIVE, BOBAK, TAYLOR & WEBER CO. LPA

(57) ABSTRACT

The present invention relates to novel compounds of the general formula (I) their pharmaceutically acceptable salts, pharmaceutically acceptable solvates, enantiomers, diastereomers and polymorphs. The invention also relates to processes for the preparation of the compounds of invention, pharmaceutical compositions containing the compounds and their use as the compounds of the invention belong to the family of NOD-like receptor family (NLR) protein NLRP3 modulators. The present invention thus relates to novel NLRP3 modulators as well as to the use of the novel inhibitor compounds in the treatment of diseases or conditions in which interleukin 1β activity is implicated.

Formula (I)

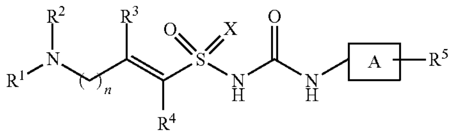

11 Claims, No Drawings

SUBTITUTED SULFONYLUREA AND SULFOXIMINEUREA DERIVATIVES

FIELD OF THE INVENTION

The present invention relates to novel compounds of the general formula (I) their pharmaceutically acceptable salts, pharmaceutically acceptable solvates, enantiomers, diastereomers and polymorphs. The invention also relates to processes for the preparation of the compounds of invention, pharmaceutical compositions containing the compounds and their use as the compounds of the invention belong to the family of NOD-like receptor family (NLR) protein NLRP3 modulators. The present invention thus relates to novel NLRP3 modulators as well as to the use of the novel inhibitor compounds in the treatment of diseases or conditions in which interleukin 1β activity is implicated.

BACKGROUND OF THE INVENTION

The NOD-like receptor family (NLR) protein NLRP3 is an intracellular signaling molecule that senses many pathogens, environmental and host-derived factors. (Wen., et. al., Immunity. 2013; 39:432-441). Activation of NLRP3 leads to binding with apoptosis associated speck-like protein containing a CARD (ASC). ASC in turn interacts with the cysteine protease caspase-1, forming a complex termed the inflammasome. This results in the activation of caspase-1, which cleaves the pro-inflammatory cytokines IL-1β and IL-18 to their active forms and mediates a type of inflammatory cell death known as pyroptosis. Other intracellular pattern recognition receptors (PRRs) are also capable of forming inflammasomes. These include other NLR family members such as NLRP1 and NLRC4 and non-NLR PRRs such as the double-stranded DNA (dsDNA) sensors absent in melanoma 2 (AIM2) and interferon, gamma inducible protein 16 (IFI16) (Latz, et. al., Nat Rev Immunol. 2013; 13:397-411). NLRP3-dependent IL-1β processing can also be activated by an indirect, non-canonical pathway downstream of caspase-1 (Lamkanfi, et. al., Cell. 2014; 157:1013-1022).

Inflammasome components such as NLRP3, ASC and caspase-1 are expressed in immune cells in the liver including Kupffer cells, infiltrating macrophages, hepatocytes, and hepatic stellate cells. Inflammasome activation is dependent on two successive signals. Signal 1 is driven by TLR and IL-1R signaling, includes expression of component proteins including NLRP3, ASC, pro-caspase-1, pro-IL-1β, and pro-IL-18. Signal 2 is provided by danger signals (DAMPS) that during NASH development are mainly released by stressed or dying hepatocytes or via a "leaky" gut (PAMPs). This process leads to oligomerization of the inflammasome components and cleavage of pro-caspase-1, leading to the release of active pro-inflammatory cytokines.

The NLRP3 inflammasome acts as a key mediator of inflammatory responses through the activation of caspase-1 leading to processing and release of the pro-inflammatory cytokines interleukin-1β (IL-1β) and interleukin-18 (IL-18). The NLRP3 inflammasome is a component of the inflammatory process and its aberrant activation is pathogenic in inherited disorders such as the rare periodic fever syndrome, cryopyrin associated periodic syndromes (CAPS), Tumor necrosis factor receptor-associated periodic syndrome (TRAPS) and complex diseases such as multiple sclerosis, type 2 diabetes, atherosclerosis, asthma, gouty arthritis, and inflammatory central nervous system (CNS) diseases including Alzheimer's and other brain diseases. (Masters, et. al., Annu Rev Immunol. 2009; 27:621-668; Strowig, et. al., Nature 2012, 481, 278-286; Guo, et. al., Nat. Med. 2015, 21, 677; Ising, et. al., Nature 2019, 575, 669-673)

Inflammation is an essential host response to infection and injury. The regulation of the pro-inflammatory cytokine interleukin-1β (IL-1β), which is central to host responses to infection, also causes tissue injury when activated inappropriately. (Dinarello, et. al., Nat. Rev. Drug Discovery 2012, 11, 633-652.) NLRP3 inflammasome activation plays a key role in each of the components including induction of pro-inflammatory signaling, hepatocellular injury and cell death, and activation of the hepatic stellate cells (HSC) that are responsible for collagen deposition and liver fibrosis. In particular, the transition from NAFLD to NASH associates with NLRP3-inflammasome activation and an increased expression of inflammasome-related components, including apoptosis-associated speck-like protein containing a carboxy-terminal CARD (ASC), caspase-1 (CASP-1) and pannexin. (Mridha, et. al., Journal of Hepatology, 2017, 66 (5), 1037-1046)

Current treatments for NLRP3 related diseases include biologic agents that target IL-1. These are the recombinant IL-1 receptor antagonist Anakinra, the neutralizing IL-1β antibody Canakinumab and the soluble decoy IL-1 receptor Rilonacept.

Suppression of IL-10 and IL-18 using NLRP3 inflammasome inhibitors would be an effective therapy during a cytokine storm and might be a plausible treatment option for diseases like severe acute respiratory syndrome (SARS), Middle East respiratory syndrome (MERS), Spanish flu, COVID19 (Coronavirus disease 2019), hepatitis C virus, chikungunya virus, influenza A virus, herpes simplex virus type 1 and Japanese encephalitis virus, where high levels of interleukin (IL)-1β and/or IL-18 have been associated with inflammation and Pathogenesis (*Lancet* 2020, 395, (10223), 497-506; *The FASEB Journal* 2020, 33, 8865-6677).

Wipo patent application No. WO98/32733, WO2001/019390, WO2014/190015, WO2016/123229 WO2016/131098 disclosed sulfonylureas derivatives and related compounds as NLRP3 inflammasome inhibitors. WO2017/017469 disclosed certain cyclic diarylboron derivatives as NLRP3 inflammasome inhibitors for the treatment of diseases or conditions in which interleukin 10 activity is implicated. Some of the recent patent applications such as WO2017/031161, WO2017/079352, WO2017/129897, WO2017/184623, WO2018/225018, WO2019/043610, WO2019/023147, WO2019/068772, WO2020/035466, WO2020/208249 WO2020/035465, WO2020/254697 also disclosed certain class of compounds as NLRP3 inhibitors.

We herein disclose novel compounds of general formula (I) which are NLRP3 modulators for the prevention and treatment of disease states mediated by NLRP3 or conditions in which interleukin 1β activity is implicated, including inflammation, gouty arthritis, type 2 diabetes, atherosclerosis, and liver fibrosis. More particularly, embodiments of the present invention are useful as therapeutics in the treatment of a variety of pathological conditions including (but not limited to) lymphoma, auto-immune diseases, heteroimmune diseases, inflammatory diseases, cancer, and neurodegenerative diseases or conditions.

SUMMARY OF THE INVENTION

The present invention discloses novel compounds as defined by the general formula (I) that are NLRP3 modulators for the prevention and treatment of disease states mediated by NLRP3 as well as treatment of diseases or conditions in which interleukin 1β activity is implicated. The compounds of the present invention are useful in the treatment of human or animal body, by inhibition of NLRP3. The compounds of this invention are therefore suitable for the prevention and treatment of disease states mediated by NLRP3.

EMBODIMENT(S) OF THE INVENTION

An embodiment of the present invention provides novel compounds represented by the general formula (I), their tautomeric forms, their enantiomers, their diastereoisomers, their stereoisomers, their pharmaceutically acceptable salts and pharmaceutical compositions containing them or their mixtures thereof.

In an another embodiment of the present invention is provided pharmaceutical compositions containing compounds of the general formula (I), their tautomeric forms, their enantiomers, their diastereoisomers, their stereoisomers, their pharmaceutically acceptable salts, or their mixtures in combination with suitable carriers, solvents, diluents and other media normally employed in preparing such compositions.

In a further embodiment is provided the use of compounds of the present invention as NLRP3 modulators, by administering a therapeutically effective and non-toxic amount of compounds of general formula (I) or their pharmaceutically acceptable compositions to the mammals.

In a still further embodiment compound of formula (I) of the present invention may be used in combination with one or more suitable pharmaceutically active agents.

In another further embodiment is provided a process for preparing the novel compounds of the present invention.

DESCRIPTION OF THE INVENTION

Accordingly, the present invention relates to the compounds of the general formula (I)

Formula (I)

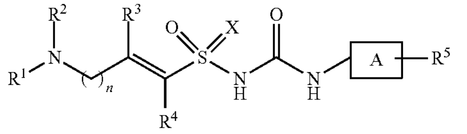

their tautomeric forms, their stereoisomers, their enantiomers, their pharmaceutically acceptable salts, and pharmaceutical compositions containing them wherein Each of $R^1$ and $R^2$ at each occurrence independently represents hydrogen, halogen, haloalkyl, cyano, optionally substituted groups selected from $(C_1\text{-}C_6)$alkyl, $(C_1\text{-}C_6)$haloalkyl, $(C_2\text{-}C_6)$alkenyl, $(C_2\text{-}C_6)$alkynyl, $(C_1\text{-}C_6)$alkoxy, $(C_3\text{-}C_7)$cycloalkyl, $(C_1\text{-}C_6)$alkyl$SO_2(C_1\text{-}C_6)$alkyl, $(C_1\text{-}C_6)$alkylN$(C_1\text{-}C_6)$alkyl, $(C_1\text{-}C_6)$alkylN$(C_3\text{-}C_7)$cycloalkyl, aryl, heteroaryl, heterocyclyl, benzyl, tert-butyloxycarbonyl, thiol, mercaptoalkyl, $SO_2(C_1\text{-}C_6)$alkyl, $SO_2(C_3\text{-}C_7)$cycloalkyl, $SO_2$-aryl, $SO_2$-heterocyclyl, $(C_1\text{-}C_6)$thioalkyl, $(C_1\text{-}C_6)$thioalkoxy, $(C_1\text{-}C_6)$alkyl$SO_2NH_2$, —$CONH_2$, —CO$(C_1\text{-}C_6)$alkyl, —CO$(C_1\text{-}C_6)$haloalkyl, CO(O)$(C_1\text{-}C_6)$alkyl, —CO-aryl, —CO-heteroaryl, —CO-heterocyclyl, 4- to 7-membered heterocyclic ring, 7- to 14-membered bicyclic heterocyclic ring system, bridged or Spiro ring system having optionally one or more than one heteroatoms; Alternatively $R^1$, $R^2$ and N together may form a saturated or partially saturated 3 to 8 membered heterocyclic ring system, 7- to 14-membered bicyclic heterocyclic ring system, bridged or spiro ring system having optionally one or more than one heteroatoms;

Each of $R^3$ and $R^4$ at each occurrence represents hydrogen, halogen, haloalkyl, cyano, nitro, amide, sulphonamide, acyl, hydroxyl, optionally substituted groups selected from $(C_1\text{-}C_6)$alkyl, $(C_1\text{-}C_6)$haloalkyl, $(C_3\text{-}C_6)$cycloalkyl, $(C_1\text{-}C_6)$alkoxy, $SO_2(C_1\text{-}C_6)$alkyl, thiol, mercapto alkyl benzyl, aryl, heteroaryl, heterocyclyl; Alternatively $R^3$ and $R^4$ may forms a bond;

X is O, N—$R^6$; wherein $R^6$ at each occurrence independently represents hydrogen, hydroxyl, halogen, nitro, cyano, haloalkyl, optionally substituted groups selected from $(C_1\text{-}C_{10})$alkyl, $(C_1\text{-}C_{10})$alkoxy, $(C_3\text{-}C_{10})$cycloalkyl, $(C_2\text{-}C_{10})$alkenyl, $(C_2\text{-}C_{10})$alkynyl, $SO_2(C_1\text{-}C_6)$alkyl, thiol, thioalkyl, thio-alkoxy, $SO_2(C_1\text{-}C_6)$alkyl, $SO(C_1\text{-}C_6)$alkyl, benzyl, aryl, heteroaryl, heterocyclyl;

n, is independently selected from integer 0-3;

$R^5$ at each occurrence independently represents hydrogen, halogen, haloalkyl, cyano, optionally substituted groups selected from $(C_1\text{-}C_6)$alkyl, $(C_1\text{-}C_6)$alkoxy, $(C_2\text{-}C_6)$alkenyl, $(C_3\text{-}C_7)$cycloalkyl, benzyl, aryl, heteroaryl, heterocyclyl, thiol, thioalkyl, thio-alkoxy, $SO_2(C_1\text{-}C_6)$alkyl, $SO(C_1\text{-}C_6)$alkyl, bridged or spiro ring system having optionally one or more than one heteroatoms;

'A' is selected from the following ring system

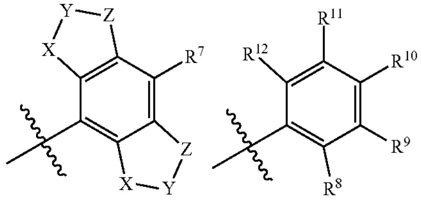

wherein X, Y, Z at each occurrence independently represents C, N, S, $SO_2$, and O, which may be optionally substituted;

Each of $R^7$, $R^8$, $R^9$, $R^{10}$, $R^{11}$ and $R^{12}$ at each occurrence are independently selected from hydrogen, halogen, cyano, amide, sulphonamide, acyl, hydroxyl, optionally substituted groups selected from $(C_1\text{-}C_6)$alkyl, $(C_1\text{-}C_6)$haloalkyl, $(C_3\text{-}C_6)$cycloalkyl, $(C_1\text{-}C_6)$alkoxy, benzyl, aryl, heteroaryl, heterocyclyl; Alternatively each of $R^8$ and $R^9$, $R^9$ and $R^{10}$, $R^{10}$ and $R^{11}$ and $R^{11}$ and $R^{12}$ wherever possible, together may form a 4 to 7 membered saturated or partially saturated ring containing from 0-2 additional heteroatoms selected from the group consisting of N, O, and $S(O)_p$; p=1-2.

When any of above defined group is substituted the substitutions on them may be selected from those described above or may be selected from hydrogen, hydroxy, cyano, halo, haloalkyl, haloalkyloxy, alkylthio, $(C_1\text{-}C_6)$alkyl, $(C_2\text{-}C_6)$alkenyl, $(C_2\text{-}C_6)$alkynyl, $(C_3\text{-}C_{10})$cycloalkyl, $C_1$—$(C_1\text{-}C_6)$alkoxy, aryl, heterocyclyl, heteroaryl, —$COR_{11}$, —$CSR_{11}$, C(O)$OR_{11}$, C(O)—$R_{11}$, —C(O)—$NR_{11}R_{12}$, —C(S)—$NR_{11}R_{12}$, —$SO_2R_{11}$ group, wherein each of, $R_{11}$ and $R_{12}$ is independently selected from hydrogen, optionally substituted group selected from $(C_1\text{-}C_6)$alkyl, $(C_2\text{-}C_6)$alkenyl, $(C_2\text{-}C_6)$alkynyl, $(C_3\text{-}C_7)$cycloalkyl, aryl, heteroaryl, heterocyclyl groups;

In a preferred embodiment each of $R^3$ and $R^4$ at each occurrence independently selected from hydrogen, halogen, optionally substituted group selected from $(C_1\text{-}C_6)$alkyl;

In a preferred embodiment $R^5$ at each occurrence independently represents hydrogen, halogen, optionally substituted group selected from $(C_1\text{-}C_6)$alkyl;

In a preferred embodiment $R^6$ at each occurrence independently represents hydrogen, cyano;

In a preferred embodiment each of $R^7$, $R^8$, $R^9$, $R^{10}$, $R^{11}$ and $R^{12}$ at each occurrence independently selected from hydrogen, halogen, hydroxy optionally substituted groups selected from $(C_1-C_6)$alkyl, $(C_1-C_6)$haloalkyl;

In a preferred embodiment, the groups, radicals described above may be selected from:

"Alkyl", as well as other groups having the prefix "alk", such as alkoxy and alkanoyl, means a carbon chain which may further be substituted with an oxygen atom as is well understood by a skilled artisan, which may further be either linear or branched, and combinations thereof, unless the carbon chain is defined otherwise. Examples of alkyl group include but not limited to methyl, ethyl, propyl, isopropyl, butyl, sec-butyl, tert.-butyl, pentyl, hexyl etc. where the specified number of carbon atoms permits e.g. from $C_{3-10}$, the term alkyl also includes cycloalkyl groups, and combinations of linear or branched alkyl chains combined with cycloalkyl structures. When no number of carbon atoms is specified, $C_{1-6}$ is intended. Substituted alkyl includes alkyl substituted with one or more moieties selected from the group consisting of halo {e.g., CI, F, Br, and I); halogenated alkyl {e.g., $CF_3$, 2-Br-ethyl, $CH_2F$, $CH_2CI$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of 'Optionally substituted'.

"Alkenyl" means carbon chains which contain at least one carbon-carbon double bond, and which may be linear or branched or combinations thereof, unless the carbon chain is defined otherwise. Examples of alkenyl include but not limited to vinyl, allyl, isopropenyl, hexenyl, pentenyl, heptenyl, 1-propenyl, 2-butenyl, 2-methyl-2-butenyl etc. where the specified number of carbon atoms permits, e.g., from $C_{5-10}$, the term alkenyl also includes cycloalkenyl groups and combinations of linear, branched and cyclic structures. When no number of carbon atoms is specified, $C_{2-6}$ is intended.

"Alkynyl" means carbon chains which contain at least one carbon-carbon triple bond, and which may be linear or branched or combinations thereof. Examples of alkynyl include ethynyl, propargyl, 3-methyl-1-pentynyl etc. When no number of carbon atoms is specified, is intended.

the "thioalkyl" group used either alone or in combination with other radicals, denotes an alkyl group, as defined above, attached to a group of formula —SR', (sulfur and its oxidized forms) where R' represents hydrogen, alkyl or aryl group, e.g. thiomethyl, methylthiomethyl, phenylthiomethyl and the like, which may be optionally substituted.

As used herein, "carbocycle" or "carbocyclic residue" is intended to mean any stable monocyclic or bicyclic or tricyclic ring, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). In a broader perspective, the term carbocycle is intended to include, wherever applicable, the groups representing cycloalkyl, phenyl and other saturated, partially saturated or aromatic residues;

The terms "cycloalkyl" and "cycloalkenyl" refers to optionally substituted, saturated and unsaturated mono-cyclic, bicyclic or tricyclic carbon groups. Where appropriate, the cycloalkyl or cycloalkenyl group may have a specified number of carbon atoms, for example, $C_3$-$C_6$ cycloalkyl or cycloalkenyl includes within its scope a carbocyclic group having 3, 4, 5 or 6 carbon atoms. Examples of such substituents may be selected from the group consisting of cyclopropyl, cyclobutyl, cyclopentyl, cyclopentenyl, cyclohexyl, cyclohexenyl, cyclohexadienyl and the like. Substituted cycloalkyl or cycloalkenyl includes substitutions with one or more moieties selected from the group consisting of halo (e.g., CI, F, Br, and I); halogenated alkyl (e.g., $CF_3$, 2-Br-ethyl, $CH_2F$, $CH_2CI$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of 'Optionally substituted'.

The "alkoxy" refers to the straight or branched chain alkoxides of the number of carbon atoms specified.

"Aryl" means a mono- or polycyclic aromatic ring system containing carbon ring atoms. The preferred aryls are monocyclic or bicyclic 6-10 membered aromatic ring systems. Phenyl and naphthyl are preferred aryls.

"Heterocyclyl" means a saturated, partially saturated or unsaturated aromatic or non-aromatic mono, bi or tricyclic radicals, containing one or more heteroatoms selected from nitrogen, sulfur and oxygen, further optionally including the oxidized forms of sulfur, namely SO & $SO_2$ Heterocyclyl systems may be attached to another moiety via any number of carbon atoms or heteroatoms of the radical and may be both saturated and unsaturated. Examples of heterocycles include tetrahydrofuran (THF), dihydrofuran, 1,4-dioxane, morpholine, 1,4-dithiane, piperazine, piperidine, 1,3-dioxolane, imidazoline, imidazolidine, pyrrolidine, pyrroline, tetrahydropyran, dihydropyran, oxathiolane, dithiolane, 1,3-dioxane, 1,3-dithiane, oxathiane, thiomorpholine, etc. The term "heterocycloalkyl" refers to a heterocyclic group as defined above connected to an alkyl group as defined above;

"Heteroaryl" means an aromatic or partially aromatic heterocycle that contains at least one ring heteroatom selected from O, S and N. Heteroaryls thus include heteroaryls fused to other kinds of rings, such as aryls, cycloalkyls, and heterocycles that are not aromatic. Examples of heteroaryl groups include; pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzthiazolyl, benzothiadiazolyl, dihydrobenzofuranyl, indolinyl, pyridazinyl, indazolyl, isoindolyl, dihydrobenzothienyl, indolinyl, pyridazinyl, indazolyl, isoindolyl, dihydrobenzothienyl, indolizinyl, cinnolinyl, phthalazinyl, quinazolinyl, napthyridinyl, carbazolyl, benzodioxolyl, quinoxalinyl, purinyl, furazanyl, isobenzylfuranyl, benzimidazolyl, benzofuranyt, benzothienyl, quinolyl, indolyl, isoquinolyl, dibenzofuranyl etc. For heterocyclyl; and heteroaryl groups, rings and ring systems containing from 3-15 carbon atoms are included, forming 1-3 rings.

The term "haloalkyl" means an alkyl structure in which at least one hydrogen is replaced with a halogen atom. In certain embodiments in which two or more hydrogen atoms are replaced with halogen atoms, the halogen atoms are all the same as one another.

the "haloalkoxy" group is selected from suitable haloalkyl, as defined above, directly attached to an oxygen atom, more preferably groups selected from fluoromethoxy, chloromethoxy, fluoroethoxy, chloroethoxy and the like;

In certain other embodiment in which two or more hydrogen atoms are replaced with halogen atoms, the halogen atoms are not all the same as one another.

"Aryloxyalkyl" means an alkyl radical substituted with aryloxy group as defined herein.

"Aryloxyaryl" means an aryl radical substituted with aryloxy group as defined herein.

"Aryloxyheteroaryl" means a heteroaryl radical substituted with aryloxy group as defined herein.

"Halo/Halogen" refers to fluorine, chlorine, bromine, iodine. Chlorine and fluorine are generally preferred.

Suitable groups and substituents on the groups may be selected from those described anywhere in the specification.

The term "substituted," as used herein, means that any one or more hydrogen on the designated atom is replaced with a selection from the indicated group, provided that the designated atom's normal valency is not exceeded, and that the substitution results in a stable compound. The term "substituted," as used herein, means that any one or more hydrogens on the designated atom is replaced with a selection from the indicated group, provided that the designated atom's normal valency is not exceeded, and that the substitution results in a stable compound.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. Such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromie, hydrochloric, hydroiodide, hydroxymaleic, hydroxynaphthoic, isethionic, lactic, lactobionic, -lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The term 'optional' or 'optionally' means that the subsequent described event or circumstance may or may not occur, and the description includes instances where the event or circumstance occur and instances in which it does not. For example, optionally substituted alkyl' means either 'alkyl' or 'substituted alkyl'. Further an optionally substituted group includes an unsubstituted group.

Unless otherwise stated in the specification, structures depicted herein are also meant to include compounds which differ only in the presence of one or more isotopically enriched atoms.

Particularly useful compounds may be selected from but not limited to the following:

(E)-N-((1,2,3,5,6,7-hexahydro-s-indacen-4-yl)carbamoyl)-3-(isopropylamino)prop-1-ene-1-sulfonamide;

(E)-3-(dimethylamino)-N-((1,2,3,5,6,7-hexahydro-s-indacen-4-yl)carbamoyl)prop-1-ene-1-sulfonamide;

(E)-N-((1,2,3,5,6,7-hexahydro-s-indacen-4-yl)carbamoyl)-3-(methyl(propyl)amino)prop-1-ene-1-sulfonamide;

(E)-N-((1,2,3,5,6,7-hexahydro-s-indacen-4-yl)carbamoyl)-3-(propylamino)prop-1-ene-1-sulfonamide;

(E)-3-((cyclopropylmethyl)amino)-N-((1,2,3,5,6,7-hexahydro-s-indacen-4-yl)carbamoyl)prop-1-ene-1-sulfonamide;

(E)-3-((cyclopropylmethyl)(methyl)amino)-N-((1,2,3,5,6,7-hexahydro-s-indacen-4-yl)carbamoyl)prop-1-ene-1-sulfonamide;

(E)-3-(ethyl(methyl)amino)-N-((1,2,3,5,6,7-hexahydro-s-indacen-4-yl)carbamoyl)prop-1-ene-1-sulfonamide;

(E)-N-((1,2,3,5,6,7-hexahydro-s-indacen-4-yl)carbamoyl)-3-(N-methylmethylsulfonamido)prop-1-ene-1-sulfonamide;

(E)-N-(3-(N-((1,2,3,5,6,7-hexahydro-s-indacen-4-yl)carbamoyl)sulfamoyl)allyl)-N-methylcyclopropanesulfonamide;

(E)-N-(3-(N-((1,2,3,5,6,7-hexahydro-s-indacen-4-yl)carbamoyl)sulfamoyl)allyl)-N-methylcyclohexanesulfonamide;

(E)-N-(3-(N-((1,2,3,5,6,7-hexahydro-s-indacen-4-yl)carbamoyl)sulfamoyl)allyl)cyclohexanesulfonamide;

(E)-3-((cyclohexylmethyl)amino)-N-((1,2,3,5,6,7-hexahydro-s-indacen-4-yl)carbamoyl)prop-1-ene-1-sulfonamide;

(E)-3-((cyclohexylmethyl)(methyl)amino)-N-((1,2,3,5,6,7-hexahydro-s-indacen-4-yl)carbamoyl)prop-1-ene-1-sulfonamide;

(E)-N-(3-(N-((1,2,3,5,6,7-hexahydro-s-indacen-4-yl)carbamoyl)sulfamoyl)allyl)-N-methylcyclohexanecarboxamide;

(E)-N-(3-(N-((1,2,3,5,6,7-hexahydro-s-indacen-4-yl)carbamoyl)sulfamoyl)allyl)-N-methylacetamide;

(E)-N-(3-(N-((1,2,3,5,6,7-hexahydro-s-indacen-4-yl)carbamoyl)sulfamoyl)allyl)-N-methylcyclopropanecarboxamide;

(E)-N-((2,6-diisopropylphenyl)carbamoyl)-3-(dimethylamino)prop-1-ene-1-sulfonamide;

(E)-N-((2,6-diisopropyl-4-methylphenyl)carbamoyl)-3-(dimethylamino)prop-1-ene-1-sulfonamide;

(E)-3-(dimethylamino)-N-((4-fluoro-2,6-diisopropylphenyl)carbamoyl)prop-1-ene-1-sulfonamide;

(E)-N-((1,2,3,5,6,7-hexahydro-s-indacen-4-yl)carbamoyl)-3-(methyl(phenyl)amino)prop-1-ene-1-sulfonamide;

(E)-N-((1,2,3,5,6,7-hexahydro-s-indacen-4-yl)carbamoyl)-3-(phenylamino)prop-1-ene-1-sulfonamide;

(E)-N-((1,2,3,5,6,7-hexahydro-s-indacen-4-yl)carbamoyl)-3-(thiazol-2-ylamino)prop-1-ene-1-sulfonamide;

(E)-N-((1,2,3,5,6,7-hexahydro-s-indacen-4-yl)carbamoyl)-3-(methyl(thiazol-2-yl)amino)prop-1-ene-1-sulfonamide;

(E)-N'-cyano-3-(dimethylamino)-N-((1,2,3,5,6,7-hexahydro-s-indacen-4-yl)carbamoyl)prop-1-ene-1-sulfonimidamide;

(E)-N'-cyano-3-(ethyl(methyl)amino)-N-((1,2,3,5,6,7-hexahydro-s-indacen-4-yl)carbamoyl)prop-1-ene-1-sulfonimidamide;

(E)-N'-cyano-3-((cyclopropylmethyl)(methyl)amino)-N-((1,2,3,5,6,7-hexahydro-s-indacen-4-yl)carbamoyl)prop-1-ene-1-sulfonimidamide;

(E)-N'-cyano-3-((cyclopropylmethyl)amino)-N-((1,2,3,5,6,7-hexahydro-s-indacen-4-yl)carbamoyl)prop-1-ene-1-sulfonimidamide;

(E)-N'-cyano-3-(dimethylamino)-N-((4-fluoro-2,6-diisopropylphenyl)carbamoyl)prop-1-ene-1-sulfonimidamide;

(E)-3-((cyclopropylmethyl)amino)-N-((1,2,3,5,6,7-hexahydro-s-indacen-4-yl)carbamoyl)prop-1-ene-1-sulfonimidamide;

(E)-3-((cyclopropylmethyl)(methyl)amino)-N-((1,2,3,5,6,7-hexahydro-s-indacen-4-yl)carbamoyl)prop-1-ene-1-sulfonimidamide;

(E)-3-(dimethylamino)-N-((1,2,3,5,6,7-hexahydro-s-indacen-4-yl)carbamoyl)prop-1-ene-1-sulfonimidamide;

(E)-3-(dimethylamino)-N-((4-fluoro-2,6-diisopropylphenyl)carbamoyl)prop-1-ene-1-sulfonimidamide;
(E)-3-(dimethylamino)-N-((1,2,3,5,6,7-hexahydro-s-indacen-4-yl)carbamoyl)-N'-methylprop-1-ene-1-sulfonimidamide;
(E)-N'-cyano-N-((1,2,3,5,6,7-hexahydro-s-indacen-4-yl)carbamoyl)-3-(methyl(oxetan-3-yl)amino)prop-1-ene-1-sulfonimidamide;
(E)-N'-cyano-N-((1,2,3,5,6,7-hexahydro-s-indacen-4-yl)carbamoyl)-3-(oxetan-3-ylamino)prop-1-ene-1-sulfonimidamide;
(E)-N-((1,2,3,5,6,7-hexahydro-s-indacen-4-yl)carbamoyl)-3-(oxetan-3-ylamino)prop-1-ene-1-sulfonimidamide;
(E)-N-((1,2,3,5,6,7-hexahydro-s-indacen-4-yl)carbamoyl)-3-(oxetan-3-ylamino)prop-1-ene-1-sulfonamide;
(E)-N-((1,2,3,5,6,7-hexahydro-s-indacen-4-yl)carbamoyl)-3-(5-methylhexahydropyrrolo[3,4-c]pyrrol-2(1H)-yl)prop-1-ene-1-sulfonamide;
(E)-N-((1,2,3,5,6,7-hexahydro-s-indacen-4-yl)carbamoyl)-3-(hexahydropyrrolo[3,4-c]pyrrol-2(1H)-yl)prop-1-ene-1-sulfonamide;
(E)-N-((1,2,3,5,6,7-hexahydro-s-indacen-4-yl)carbamoyl)-3-(5-(methylsulfonyl)hexahydropyrrolo[3,4-c]pyrrol-2(1H)-yl)prop-1-ene-1-sulfonamide;
(E)-N-((1,2,3,5,6,7-hexahydro-s-indacen-4-yl)carbamoyl)-3-(hexahydropyrrolo[3,4-c]pyrrol-2(1H)-yl)prop-1-ene-1-sulfonamide;
(E)-N-((1,2,3,5,6,7-hexahydro-s-indacen-4-yl)carbamoyl)-3-(tetrahydro-1H-furo[3,4-c]pyrrol-5(3H)-yl)prop-1-ene-1-sulfonamide;
(E)-N-((1,2,3,5,6,7-hexahydro-s-indacen-4-yl)carbamoyl)-3-(3,4,5,6-tetrahydropyrrolo[3,4-c]pyrrol-2(1H)-yl)prop-1-ene-1-sulfonamide;
(E)-N-((1,2,3,5,6,7-hexahydro-s-indacen-4-yl)carbamoyl)-3-(5-(methylsulfonyl)-3,4,5,6-tetrahydropyrrolo[3,4-c]pyrrol-2(1H)-yl)prop-1-ene-1-sulfonamide.

or pharmaceutically acceptable salts of any of the compounds above.

Following is a list of abbreviations used in the description of the preparation of the compounds of the present invention:

μg: microgram
$^1$H NMR: Proton nuclear magnetic resonance
bs: broad singlet
$CDCl_3$: Deuterated chloroform
$CHCl_3$: Chloroform
d: doublet
DAMP: damage-associated molecular pattern;
DBU: 1,8-Diazabicyclo(5.4.0)undec-7-ene
DCM: Dichloromethane
dd: doublet of doublet
DMAC: N,N-(Dimethylacetamide)
DMAP: 4-(Dimethylamino) pyridine
DMF: N,N-Dimethyl formamide
DMSO: Dimethyl sulfoxide
dt: doublet of triplet
EDTA: Ethylenediaminetertraacetic acid
EtOAc: Ethyl acetate
EtOH: Ethanol
HCl(g): Hydrogen chloride (gas)
IL1β: Interleukin 1 beta
$K_2CO_3$: Potassium carbonate
m: multiplet
MeOH: Methanol
mmol: millimoles
MS: Mass spectrum
$N_2$: Nitrogen $Na_2CO_3$: Sodium carbonate
ng: nanogram
NIS: N-iodosuccinimide
PAMP: pathogen-associated molecular pattern;
PMA=Phorbol 12-myristate 13-acetate
$POCl_3$: Phosphorylchloride
RM: reaction mixture
r.t, RT: room temperature
s: singlet
t: Triplet
td: triplet of doublet
THF: Tetrahydrofuran
TLC: Thin layer chromatography
TLR: Toll-like receptor.
TNF α: Tumor necrosis factor alpha General Process for Preparation The novel compounds of the present invention can be prepared using the reactions and techniques described below, together with conventional techniques known to those skilled in the art of organic synthesis, or variations thereon as appreciated by those skilled in the art.

The reactions can be performed in solvents appropriate to the reagents and materials employed and suitable for the transformations being affected. Preferred methods include, but not limited to those described below, where all symbols are as defined earlier unless and otherwise defined below.

The compounds of the general formula (I) can be prepared as described in schemes below along with suitable modifications/variations which are well within the scope of a person skilled in the art.

Scheme 1

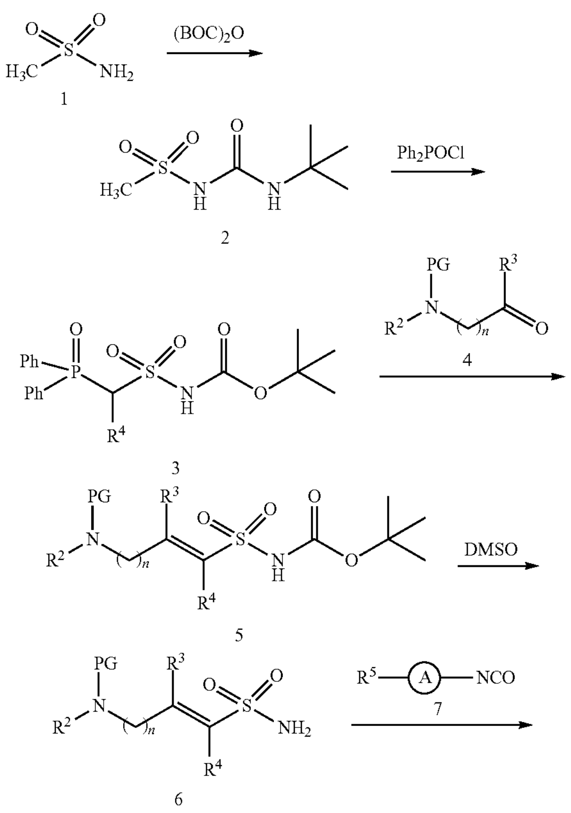

-continued

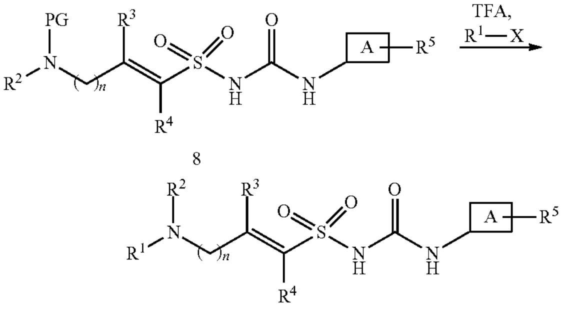

8

(I)

Wherein each of 'A', $R^1$, $R^2$, $R^3$, $R^4$ and $R^5$ are as defined earlier. Compound (2) can be prepared by variety of methods familiar to those skilled in art using a reagent like Boc anhydride from commercially available methane sulfonamide (1). Compound (2) on treatment with diphenylphosphinic chloride under suitable conditions and appropriate solvents provided compound (3) (ref. Synthesis 2003, 15, 2321-24). Compound (3) on treatment with aldehyde or ketone derivative (4) under suitable conditions in presence of base like sodium hydride and appropriate solvent provided compound (5), which can be deprotected under suitable conditions to afford compound (6). Compound (6) on treatment with isocyanato derivative (7) under suitable conditions in presence of base like sodium hydride and appropriate solvent to afford compound (8). Deprotection of the protecting group of compound (8) followed by treatment with appropriate substituted aldehyde or ketone or treatment with alkyl halide resulted in compound of formula (I).

Specific reaction conditions, solvents and other parameters necessary for carrying out the process steps as described above are well within the capabilities of a person skilled in the art.

The invention is further illustrated by the following non-limiting examples which describe the preferred way of carrying out the present invention. These are provided without limiting the scope of the present invention in any way.

$^1H$ NMR spectral data given in the examples (vide infra) are recorded using a 400 MHz spectrometer (Bruker AVANCE-400) and reported in δ scale. Until and otherwise mentioned the solvent used for NMR is $CDCl_3$ using TMS as the internal standard.

Example-1

Preparation of (E)-N-((1,2,3,5,6,7-hexahydro-s-indacen-4-yl)carbamoyl)-3-(isopropylamino)prop-1-ene-1-sulfonamide

Intermediate-1a: Preparation of tert-butyl (E)-((3-((tert-butoxycarbonyl)amino)prop-1-en-1-yl)sulfonyl)carbamate

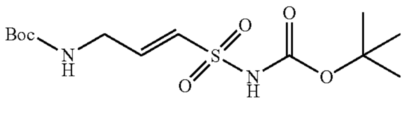 [SMILES: CC(C)(C)OC(=O)NC/C=C/S(=O)(=O)NC(=O)OC(C)(C)C]

A 250 mL, three neck, round-bottomed flask was equipped with magnetic stirrer, N2 balloon, thermos-pocket, dry ice bath. tert-butyl ((diphenylphosphoryl)methyl)sulfonylcarbamate (Synthesis 2003, 15, 2321-24) (1 Eq.) was dissolved in DMF (100 ml) under Nitrogen atmosphere. It was cooled to −20° C. and added NaH (2.2 eq.). It was gradually warmed to 25° C. and stirred for 30 min. Again cooled to −20° C. and a solution of tert-butyl (2-oxoethyl) carbamate (CAS No.: 89711-08-0) (1.2 eq) in DMF was added dropwise over a period of 1 h at −20° C. After the addition reaction mixture was warmed to r.t. and further stirred for 17 h. Reaction mixture was cooled to 0° C. and acidified with saturated citric acid solution (30 mL), and water (200 mL). Reaction mixture were extracted with ethyl acetate, organic layers were collected and dried to yield, tert-butyl (E)-((3-((tert-butoxycarbonyl)amino)prop-1-en-1-yl)sulfonyl)carbamate (25% yield).

$^1H$ NMR (400 MHz, DMSO-$d_6$): δ=11.28 (s, 1H), 7.29 (t, J=5.6 Hz, 1H), 6.76-6.70 (m, 1H), 6.58 (d, J=15.2 Hz, 1H), 3.88-3.70 (m, 2H), 1.41 (s, 9H), 1.39 (s, 9H); MS (TOF): m/z (%)=359.1603 (80%) $(M+Na)^+$, 335.1516 (100%) (M−1)

Intermediate-1b: Preparation of tert-butyl (E)-((3-((tert-butoxycarbonyl)amino)-3-methylbut-1-en-1-yl)sulfonyl)carbamate

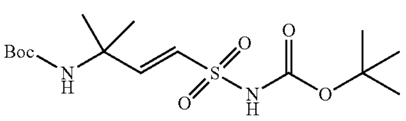 [SMILES: CC(C)(/C=C/S(=O)(=O)NC(=O)OC(C)(C)C)NC(=O)OC(C)(C)C]

Intermediate-1b was also prepared as per the procedure described for synthesis of Intermediate-1a using tert-butyl (2-methyl-1-oxopropan-2-yl)carbamate (CAS No.: 109608-77-7).

$^1H$ NMR (400 MHz, DMSO-$d_6$): δ=11.25 (s, 1H), 7.07 (s, 1H), 6.84 (d, J=15.6 Hz, 1H), 6.45 (d, J=15.2 Hz, 1H), 1.41 (s, 9H), 1.37 (s, 9H), 1.31 (s, 6H); MS (TOF): m/z (%)=363.1556 (80%) $(M+Na)^+$.

Intermediate-2a: Preparation of tert-butyl (E)-(3-sulfamoylallyl)carbamate

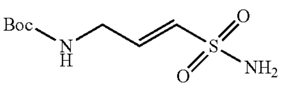

Intermediate 1 (1 eq.) was dissolved in DMSO (30 ml) & heated to 80° C. for 2 h (disappearance of the starting material was monitored by TLC). The reaction was cooled, poured into water (100 ml) & extracted with EtOAc (3×100 ml). The solvent was concentrated in vacuo & purified by column chromatography on silica gel (50% EtOAc: n-Hexane) to give product tert-butyl (E)-(3-sulfamoylallyl) carbamate (89% yield).

$^1H$ NMR (400 MHz, DMSO-$d_6$): δ=7.24 (t, J=5.6 Hz, 1H), 6.99 (s, 2H), 6.49-6.38 (m, 2H), 3.74-3.71 (m, 2H), 1.39 (s, 9H); MS (TOF): m/z (%)=259.0998 (100%) $(M+Na)^+$, 2.350928 (40%) (M−1).

Intermediate-2b: Preparation of tert-butyl (E)-(2-methyl-4-sulfamoylbut-3-en-2-yl)carbamate

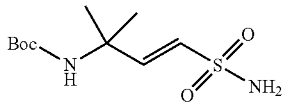 [SMILES: CC(C)(/C=C/S(N)(=O)=O)NC(=O)OC(C)(C)C]

Intermediate-2b was also prepared as per the procedure described for synthesis of Intermediate-2a using tert-butyl (E)-((3-((tert-butoxycarbonyl)amino)-3-methylbut-1-en-1-yl)sulfonyl)carbamate.

$^1$H NMR (400 MHz, DMSO-$d_6$): δ=6.96 (s, 3H), 6.60 (d, J=15.2 Hz, 1H), 6.27 (d, J=15.2 Hz, 1H), 1.39 (s, 9H), 1.30 (s, 6H); MS (TOF): m/z (%)=287.1022 (50%) $(M+Na)^+$.

Intermediate-3: Preparation of tert-butyl (E)-(3-(N-((1,2,3,5,6,7-hexahydro-s-indacen-4-yl)carbamoyl) sulfamoyl)allyl)carbamate

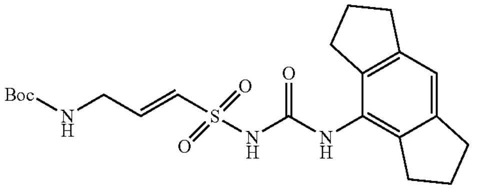 [SMILES: CC(C)(C)OC(=O)NC/C=C/S(=O)(=O)NC(=O)Nc1c2c(cc3c1CCC3)CCC2]

To a solution of the sulfonamide [Intermediate 2] (1 eq.) in DMF (220 ml) at 0° C. was added DBU (2.2 eq.). The reaction was allowed to warm to r.t. and stirred for 30 min. 4-isocyanato-1,2,3,5,6,7-hexahydro-s-indacene (1.2 eq.) was added portionwise at 0° C. the reaction was warm to r.t. and stirred overnight. The reaction was acidified using 50% aq.citric acid up to pH=2.0 the diluted with water (1500 ml), precipitate was filtered through Buchner funnel & dried to give product (76% yield).

1H NMR (400 MHz, DMSO-$d_6$): δ=10.49 (brs, 1H), 8.09 (s, 1H), 7.28 (t, J=5.6 Hz, 1H), 6.96 (s, 1H), 6.78-6.72 (m, 1H), 6.67 (d, J=15.6 Hz, 1H), 3.96-3.85 (m, 2H), 2.81 (t, J=7.2 Hz, 4H), 2.01 (t, J=7.2 Hz, 4H), 2.01-1.94 (m, 4H), 1.42 (s, 9H); MS (ESI): m/z (%)=434.1724(100%) (M−1).

Intermediate-4 Preparation of (E)-3-amino-N-((1,2,3,5,6,7-hexahydro-s-indacen-4-yl)carbamoyl)prop-1-ene-1-sulfonamide2,2,2-trifluoroacetate

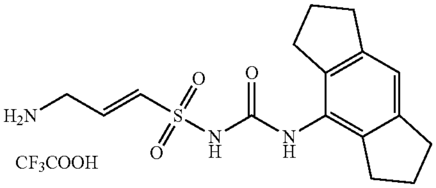 [SMILES: "CF3COOH" ; NC/C=C/S(=O)(=O)NC(=O)Nc1c2c(cc3c1CCC3)CCC2]

To solution of Intermediate 3 (1 eq.) in DCM (2.5 ml) added TFA (10 eq.) at 0° C. The reaction was warmed to r.t. & stirred further for 3 h. The reaction mixture was concentrated in vacuo & purified to give product.

$^1$H NMR (400 MHz, DMSO-$d_6$): δ=10.87 (brs, 1H), 8.14 (s, 1H), 8.02 (s, 3H), 7.05 (d, J=15.2 Hz, 1H), 6.97 (s, 1H), 6.80-6.74 (m, 1H), 3.89-3.69 (m, 2H), 2.81 (t, J=7.2 Hz, 4H), 2.01 (t, J=7.2 Hz, 4H), 2.01-1.94 (m, 4H); MS (ESI): m/z (%)=336.1316 (100%) $(M+H)^+$, 334.1172 (100%) (M−1).

Example-1

(E)-N-((1,2,3,5,6,7-hexahydro-s-indacen-4-yl)carbamoyl)-3-(isopropylamino)prop-1-ene-1-sulfonamide

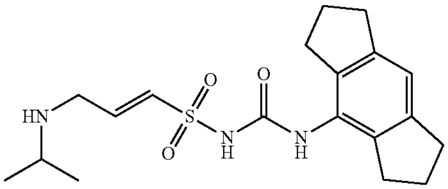 [SMILES: CC(C)NC/C=C/S(=O)(=O)NC(=O)Nc1c2c(cc3c1CCC3)CCC2]

To a solution of Intermediate 4 (1 eq.) in MeOH (7.0 mL) at r.t. was added triethyl amine (2.5 eq.) & stirred for 5 min. Acetone (3.5 eq.) was added at r.t. and stirred for 2 h. Thereafter reaction mixture was treated with $NaCNBH_3$ (1.5 eq.) portion wise at 0° C. then reaction mixture was allowed to warm to r.t. stirred overnight. The reaction mixture was purified by prep. HPLC to give pure product.

$^1$H NMR (400 MHz, DMSO-$d_6$): δ=8.28 (br s, 1H), 7.51 (s, 1H), 6.97 (d, J=15.6 Hz, 1H), 6.80 (s, 1H), 6.36-6.29 (m, 1H), 3.64 (d, J=6.4 Hz, 2H), 3.20-3.14 (m, 1H), 2.77 (t, J=7.6 Hz, 4H), 2.70 (t, J=7.2 Hz, 4H), 1.96-1.88 (m, 4H), 1.16 (d, J=6.4 Hz, 6H); MS (ESI): m/z (%)=378.1787 (100%) $(M+H)^+$, 376.1640 (100%) (M−1).

Using appropriate starting materials and suitable modifications of the process described in example 1, including suitable addition and/or deletion of steps as may be necessary which are well within the scope of a person skilled in the art, the following compounds were prepared in an analogues manner.

Example-2

(E)-3-(dimethylamino)-N-((1,2,3,5,6,7-hexahydro-s-indacen-4-yl)carbamoyl)prop-1-ene-1-sulfonamide To a solution of Intermediate 4 (1 eq.) in MeOH (7.0 mL) at r.t. was added triethyl amine (2.5 eq.) & stirred for 5 min. p-formaldehyde (5 eq.) was added at r.t. and stirred for 2 h. Thereafter reaction mixture was treated with $NaCNBH_3$ (2.5 eq.) portion wise at 0° C. then reaction mixture was allowed to warm to r.t. stirred overnight. The reaction mixture was purified by prep. HPLC to give pure product.

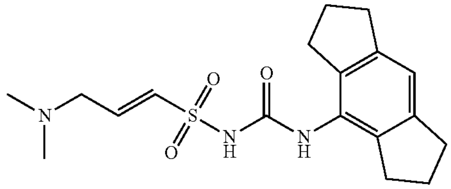 [SMILES: CN(C)C/C=C/S(=O)(=O)NC(=O)Nc1c2c(cc3c1CCC3)CCC2]

$^1$H NMR (400 MHz, DMSO-$d_6$): δ=10.22 (brs, 1H), 7.94 (s, 1H), 6.91 (s, 1H), 6.86 (d, J=15.2 Hz, 1H), 6.62-6.55 (m, 1H), 3.27 (t, J=6.0 Hz, 2H), 2.79 (t, J=7.2 Hz, 4H), 2.67 (t, J=7.2 Hz, 4H), 2.30 (s, 6H), 1.99-1.91 (m, 4H); MS (ESI): m/z (%)=364.1513 (100%) $(M+H)^+$.

Example-3

(E)-3-amino-N-((1,2,3,5,6,7-hexahydro-s-indacen-4-yl)carbamoyl)prop-1-ene-1-sulfonamide 2,2,2-trifluoroacetate

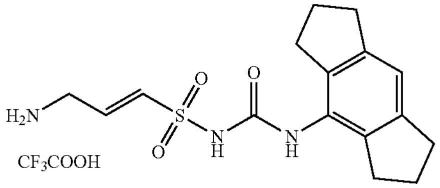 [SMILES: "CF3COOH" ; NC/C=C/S(=O)(=O)NC(=O)Nc1c2c(cc3c1CCC3)CCC2]

$^1$H NMR (400 MHz, DMSO-$d_6$): δ=10.87 (brs, 1H), 8.14 (s, 1H), 8.02 (s, 3H), 7.05 (d, J=15.2 Hz, 1H), 6.97 (s, 1H), 6.80-6.74 (m, 1H), 3.89-3.69 (m, 2H), 2.81 (t, J=7.2 Hz, 4H), 2.01 (t, J=7.2 Hz, 4H), 2.01-1.94 (m, 4H); MS (TOF): m/z (%)=336.1316 (100%) $(M+H)^+$, 334.1172 (100%) (M−1).

Example-4

(E)-3-(dipropylamino)-N-((1,2,3,5,6,7-hexahydro-s-indacen-4-yl)carbamoyl)prop-1-ene-1-sulfonamide

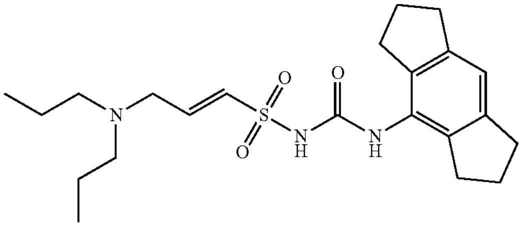 [SMILES: CCCN(C/C=C/S(=O)(=O)NC(=O)Nc1c2c(cc3c1CCC3)CCC2)CCC]

$^1$H NMR (400 MHz, DMSO-$d_6$): δ=10.27 (brs, 1H), 8.02 (s, 1H), 6.94 (s, 1H), 6.88 (d, J=15.2 Hz, 1H), 6.67-6.37 (m, 1H), 3.45-3.28 (m, 2H), 2.80 (t, J=7.2 Hz, 4H), 2.67 (t, J=7.2 Hz, 4H), 2.41 (t, J=6.8 Hz, 4H), 2.00-1.92 (m, 4H), 1.45-1.36 (m, 4H), 0.82 (t, J=7.2 Hz, 6H); MS (TOF): m/z (%)=420.2633 (100%) $(M+H)^+$, 418.2245 (100%) (M−1).

Example-5

(E)-N-((1,2,3,5,6,7-hexahydro-s-indacen-4-yl)carbamoyl)-3-(isopropyl(methyl)amino)prop-1-ene-1-sulfonamide

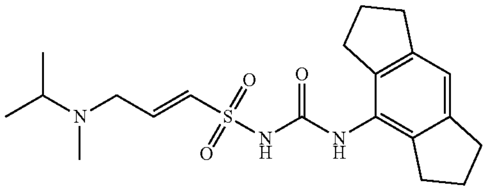 [SMILES: CC(C)N(C)C/C=C/S(=O)(=O)NC(=O)Nc1c2c(cc3c1CCC3)CCC2]

$^1$H NMR (400 MHz, DMSO-$d_6$): δ=7.89 (s, 1H), 6.90-6.86 (m, 2H), 6.61-6.54 (m, 1H), 3.60-3.37 (m, 2H), 3.02-2.99 (m, 1H), 2.79 (t, J=7.2 Hz, 4H), 2.67 (t, J=7.2 Hz, 4H), 2.27 (s, 3H), 1.99-1.91 (m, 4H), 1.01 (d, J=6.8 Hz, 6H); MS (TOF): m/z (%)=392.1983 (100%) $(M+H)^+$, 390.1817 (100%) (M−1).

Example-6

(E)-3-(dimethylamino)-N-((1,2,3,5,6,7-hexahydro-s-indacen-4-yl)carbamoyl)-3-methylbut-1-ene-1-sulfonamide

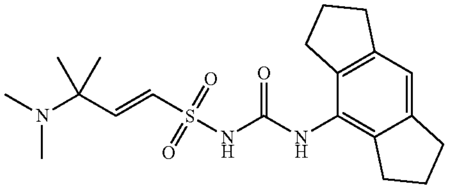 [SMILES: CN(C)C(C)(C)/C=C/S(=O)(=O)NC(=O)Nc1c2c(cc3c1CCC3)CCC2]

$^1$H NMR (400 MHz, DMSO-$d_6$): δ=7.88 (s, 1H), 6.90 (s, 1H), 6.71 (d, J=15.6 Hz, 1H), 6.60 (d, J=15.2 Hz, 1H), 2.77 (t, J=7.2 Hz, 4H), 2.67 (t, J=7.2 Hz, 4H), 2.32 (s, 6H), 1.98-1.91 (m, 4H), 1.21 (s, 6H); MS (TOF): m/z (%)=392.1992 (100%) $(M+H)^+$, 390.1819 (100%) (M−1).

Example-7 tert-butyl (E)-(4-(N-((1,2,3,5,6,7-hexahydro-s-indacen-4-yl)carbamoyl)sulfamoyl)-2-methylbut-3-en-2-yl)carbamate

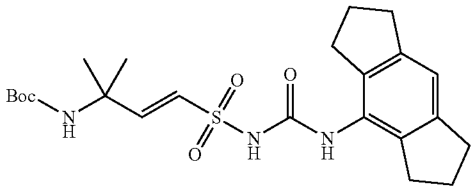 [SMILES: CC(C)(/C=C/S(=O)(=O)NC(=O)Nc1c2c(cc3c1CCC3)CCC2)NC(=O)OC(C)(C)C]

$^1$H NMR (400 MHz, DMSO-$d_6$): δ=9.05 (s, 1H), 7.81 (s, 1H), 6.95 (s, 1H), 6.89 (s, 1H), 6.72 (d, J=16.0 Hz, 1H), 6.56 (d, J=15.2 Hz, 1H), 2.79 (t, J=7.2 Hz, 4H), 2.79 (t, J=7.2 Hz, 4H), 2.68 (t, J=7.2 Hz, 4H), 1.98-1.91 (m, 4H), 1.36 (s, 9H), 1.21 (s, 6H); MS (TOF): m/z (%)=462.2029 (100%) (M−1).

Example-8

(E)-3-amino-N-((1,2,3,5,6,7-hexahydro-s-indacen-4-yl)carbamoyl)-3-methylbut-1-ene-1-sulfonamide 2,2,2-trifluoroacetate

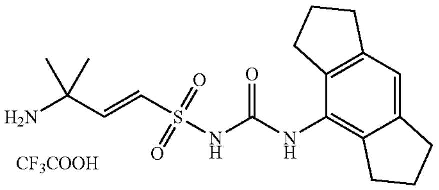 [SMILES: "CF3COOH" ; CC(C)(N)/C=C/S(=O)(=O)NC(=O)Nc1c2c(cc3c1CCC3)CCC2]

$^1$H NMR (400 MHz, DMSO-$d_6$): δ=10.90 (brs, 1H), 8.42 (s, 1H), 8.32 (s, 1H), 7.81 (s, 1H), 6.97-6.86 (m, 3H), 2.81 (t, J=7.2 Hz, 4H), 2.69 (t, J=7.2 Hz, 4H), 2.01-1.90 (m, 4H), 1.41 (s, 6H); MS (TOF): m/z (%)=364.1659 (100%) $(M+H)^+$, 364.1659 (10%) (M−1).

Example-9

(E)-N-((1,2,3,5,6,7-hexahydro-s-indacen-4-yl)carbamoyl)-3-((tetrahydro-2H-pyran-4-yl)amino)prop-1-ene-1-sulfonamide

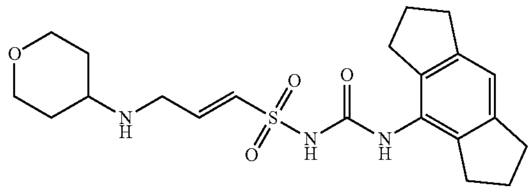

$^1$H NMR (400 MHz, DMSO-$d_6$): δ=7.68 (s, 1H), 6.93 (d, J=15.2 Hz, 1H), 6.85 (s, 1H), 6.52-6.46 (m, 1H), 3.85-3.82 (m, 2H), 3.60 (d, J=5.6 Hz, 2H), 3.26-3.20 (m, 2H), 3.04-2.90 (m, 1H), 2.78 (t, J=7.2 Hz, 4H), 2.70 (t, J=7.2 Hz, 4H), 1.97-1.90 (m, 4H), 1.84-1.81 (m, 2H), 1.42-1.34 (m, 2H); MS (TOF): m/z (%)=420.1931 (100%) $(M+H)^+$.

Example-10

(E)-N-((1,2,3,5,6,7-hexahydro-s-indacen-4-yl)carbamoyl)-3-((1-methylpiperidin-4-yl)amino)prop-1-ene-1-sulfonamide

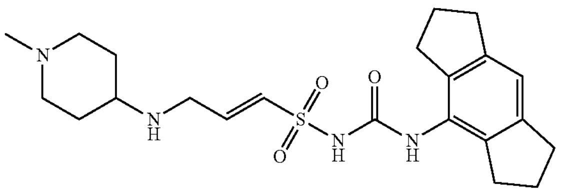 [SMILES: CN1CCC(NC/C=C/S(=O)(=O)NC(=O)Nc2c3c(cc4c2CCC4)CCC3)CC1]

$^1$H NMR (400 MHz, DMSO-$d_6$): δ=7.61 (s, 1H), 6.88 (d, J=15.6 Hz, 1H), 6.85 (s, 1H), 6.42 (dt, J=15.2 Hz, J=6.0 Hz, 1H), 3.51 (d, J=5.6 Hz, 2H), 2.92-2.89 (m, 2H), 2.80 (t, J=7.2 Hz, 4H), 2.72 (t, J=7.2 Hz, 4H), 2.29 (s, 3H), 2.21-2.08 (m, 2H), 2.01-1.94 (m, 4H), 1.93-1.87 (m, 3H), 1.48-1.40 (m, 2H); MS (TOF): m/z (%)=433.2725 (100%) $(M+H)^+$, 431.2362 (20%) (M−1).

Example-11

(E)-N-((1,2,3,5,6,7-hexahydro-s-indacen-4-yl)carbamoyl)-3-((tetrahydro-2H-thiopyran-4-yl)amino)prop-1-ene-1-sulfonamide

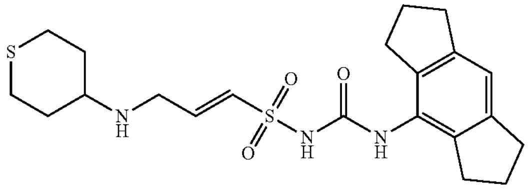 [SMILES: O=C(Nc1c2c(cc3c1CCC3)CCC2)NS(=O)(=O)/C=C/CNC1CCSCC1]

$^1$H NMR (400 MHz, DMSO-$d_6$): δ=7.74 (s, 1H), 6.92 (d, J=15.2 Hz, 1H), 6.87 (s, 1H), 6.54-6.51 (m, 1H), 3.57 (d, J=5.2 Hz, 2H), 2.79 (t, J=7.2 Hz, 4H), 2.71 (t, J=7.2 Hz, 4H), 2.67-2.63 (m, 2H), 2.57-2.51 (m, 3H), 2.18-2.16 (m, 2H), 1.99-1.92 (m, 4H), 1.52-1.42 (m, 2H); MS (TOF): m/z (%)=436.2359 (100%) $(M+H)^+$, 434.1904 (50%) (M−1).

Example-12

((E)-N-((1,2,3,5,6,7-hexahydro-s-indacen-4-yl)carbamoyl)-3-(isopropylamino)-3-methylbut-1-ene-1-sulfonamide

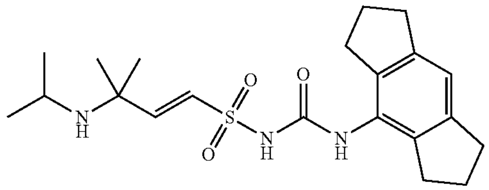

$^1$H NMR (400 MHz, DMSO-$d_6$): δ=7.55 (s, 1H), 6.83-6.80 (m, 2H), 6.47 (d, J=16.0 Hz, 1H), 3.23-3.14 (m, 1H), 2.77 (t, J=7.2 Hz, 4H), 2.69 (t, J=7.2 Hz, 4H), 1.96-1.89 (m, 4H), 1.37 (s, 6H), 1.13 (d, J=6.4 Hz, 6H); MS (TOF): m/z (%)=406.2135 (100%) $(M+H)^+$, 404.1985 (30%) (M−1).

Example-13

(E)-3-(cyclohexylamino)-N-((1,2,3,5,6,7-hexahydro-s-indacen-4-yl)carbamoyl)-3-methylbut-1-ene-1-sulfonamide

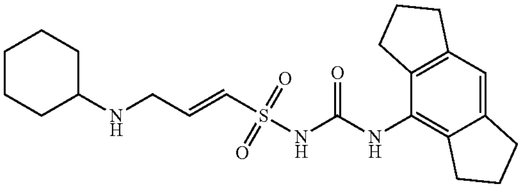 [SMILES: O=C(Nc1c2c(cc3c1CCC3)CCC2)NS(=O)(=O)/C=C/CNC1CCCCC1]

$^1$H NMR (400 MHz, DMSO-$d_6$): δ=7.58 (s, 1H), 6.81-6.77 (m, 2H), 6.48 (d, J=15.2 Hz, 1H), 2.82-2.80 (m, 1H), 2.75 (t, J=7.2 Hz, 4H), 2.67 (t, J=7.2 Hz, 4H), 1.94-1.87 (m, 4H), 1.82-1.73 (m, 2H), 1.67-1.52 (m, 2H), 1.49-1.41 (m,

1H), 1.32 (s, 6H), 1.21-1.11 (m, 4H), 1.03-1.01 (m, 1H); MS (TOF): m/z (%)=446.2445 (100%) (M+H)+, 444.2301 (300%) (M−1).

Example-14

((E)-3-amino-N-((1,2,3,5,6,7-hexahydro-s-indacen-4-yl)carbamoyl)-3-methylbut-1-ene-1-sulfonamide

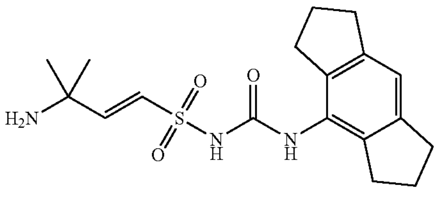 [SMILES: CC(C)(N)/C=C/S(=O)(=O)NC(=O)Nc1c2c(cc3c1CCC3)CCC2]

1H NMR (400 MHz, DMSO-d6): δ=7.93 (brs, 2H), 7.39 (s, 1H), 6.85 (d, J=15.6 Hz, 1H), 6.76 (s, 1H), 6.36 (d, J=15.6 Hz, 1H), 2.74 (t, J=7.2 Hz, 4H), 2.68 (t, J=7.2 Hz, 4H), 1.93-1.85 (m, 4H), 1.31 (m, 6H); MS (TOF): m/z (%)=364.1665 (100%) $(M+H)^+$, 362.1531 (10%) (M−1).

Example-15

(E)-N-((1,2,3,5,6,7-hexahydro-s-indacen-4-yl)carbamoyl)-3-(methyl(1-methylpiperidin-4-yl)amino)prop-1-ene-1-sulfonamide

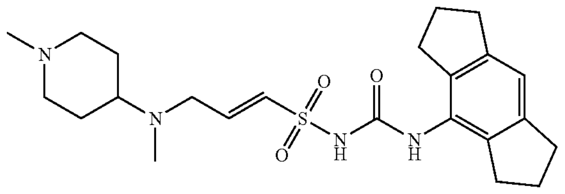 [SMILES: CN1CCC(N(C)C/C=C/S(=O)(=O)NC(=O)Nc2c3c(cc4c2CCC4)CCC3)CC1]

$^1$H NMR (400 MHz, DMSO-$d_6$): δ=7.65 (s, 1H), 6.83 (s, 1H), 6.71 (d, J=15.6 Hz, 1H), 6.39-6.32 (m, 1H), 3.18 (d, J=5.2 Hz, 2H), 2.93-2.90 (m, 2H), 2.78 (t, J=7.2 Hz, 4H), 2.69 (t, J=7.2 Hz, 4H), 2.24 (s, 3H), 2.17-2.12 (m, 4H), 1.97-1.91 (m, 6H), 1.71-1.68 (m, 2H), 1.54-1.46 (m, 2H); MS (TOF): m/z (%)=447.2401 (100%) $(M+H)^+$, 445.2269 (20%) (M−1).

Example-16

(E)-3-(diethylamino)-N-((1,2,3,5,6,7-hexahydro-s-indacen-4-yl)carbamoyl)-3-methylbut-1-ene-1-sulfonamide

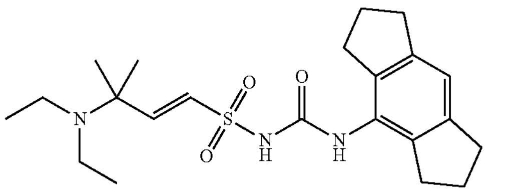 [SMILES: CCN(CC)C(C)(C)/C=C/S(=O)(=O)NC(=O)Nc1c2c(cc3c1CCC3)CCC2]

$^1$H NMR (400 MHz, DMSO-$d_6$): δ=7.68 (s, 1H), 6.90 (s, 1H), 6.67 (d, J=15.6 Hz, 1H), 6.60 (d, J=15.6 Hz, 1H), 2.80 (t, J=7.2 Hz, 4H), 2.72 (t, J=7.2 Hz, 4H), 2.64-2.54 (m, 4H), 1.99-1.92 (m, 4H), 1.19 (s, 6H), 1.00 (t, J=6.4 Hz, 6H); MS (TOF): m/z (%)=420.2287 (100%) $(M+H)^+$, 418.2140 (20%) (M−1).

Example-17

(E)-N-((1,2,3,5,6,7-hexahydro-s-indacen-4-yl)carbamoyl)-3-(piperidin-1-yl)prop-1-ene-1-sulfonamide

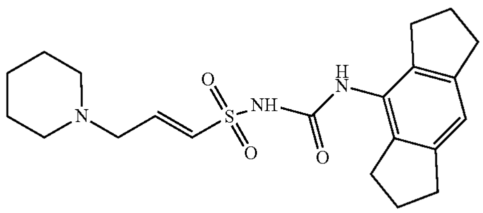 [SMILES: O=C(Nc1c2c(cc3c1CCC3)CCC2)NS(=O)(=O)/C=C/CN1CCCCC1]

$^1$H NMR (400 MHz, DMSO-$d_6$): δ=7.85 (s, 1H), 6.88 (s, 1H), 6.79 (d, J=15.6 Hz, 1H), 6.52 (d, J=3.6 Hz, 1H), 2.79 (t, J=7.2 Hz, 4H), 2.67 (t, J=7.2 Hz, 4H), 1.93 (d, J=13.6 Hz, 7H), 1.51 (m, 4H), 1.39 (m, 4H); MS (ESI): m/z (%)=404.19 (100%) (M+1).

Example-18

(E)-N-((1,2,3,5,6,7-hexahydro-s-indacen-4-yl)carbamoyl)-3-(pyrrolidin-1-yl)prop-1-ene-1-sulfonamide

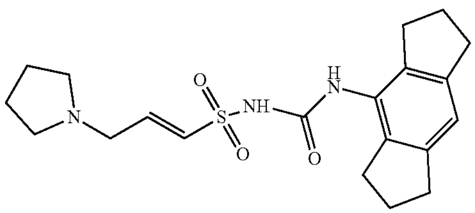 [SMILES: O=C(Nc1c2c(cc3c1CCC3)CCC2)NS(=O)(=O)/C=C/CN1CCCC1]

$^1$H NMR (400 MHz, DMSO-$d_6$): δ=10.22 (s, 1H), 7.82 (s, 1H), 7.00 (s, 1H), 6.91 (d, J=15.6 Hz, 1H), 6.57 (d, J=8.4 Hz, 1H), 3.47 (m, 3H), 2.79 (t, J=7.2 Hz, 4H), 2.68 (t, J=7.2 Hz, 4H), 1.95 (m, 4H), 1.76 (s, 4H); MS (ESI): m/z (%)=390.18 (100%) (M+1).

Example-19

(E)-N-((1,2,3,5,6,7-hexahydro-s-indacen-4-yl)carbamoyl)-3-(methyl(tetrahydro-2H-pyran-4-yl)amino)prop-1-ene-1-sulfonamide

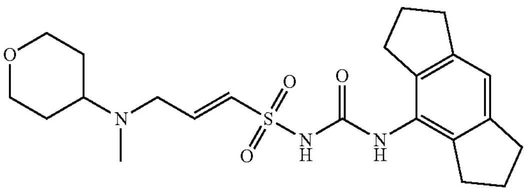 [SMILES: CN(C/C=C/S(=O)(=O)NC(=O)Nc1c2c(cc3c1CCC3)CCC2)C1CCOCC1]

$^1$H NMR (400 MHz, DMSO-$d_6$): δ=10.28 (brs, 1H), 8.02 (s, 1H), 6.92 (s, 1H), 6.84 (d, J=15.2 Hz, 1H), 6.71-6.58 (m, JH), 3.85-3.82 (m, 2H), 3.48-3.29 (m, 2H), 3.23-3.17 (m, 2H), 2.78 (t, J=7.2 Hz, 4H), 2.65 (t, J=7.2 Hz, 4H), 2.59-2.54 (m, 1H), 2.19 (s, 3H), 1.98-1.90 (m, 4H), 1.64-1.61 (m, 2H), 1.45-1.34 (m, 2H); MS (TOF): m/z (%)=434.2078 (100%) (M+H)+, 432.1949 (30%) (M−1).

Example-20

(E)-3-(ethyl(methyl)amino)-N-((1,2,3,5,6,7-hexahydro-s-indacen-4-yl)carbamoyl)-3-methylbut-1-ene-1-sulfonamide

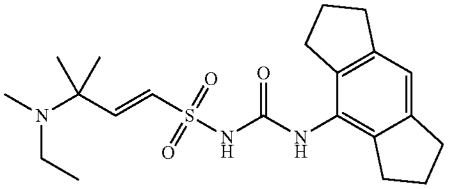 [SMILES: CCN(C)C(C)(C)/C=C/S(=O)(=O)NC(=O)Nc1c2c(cc3c1CCC3)CCC2]

$^1$H NMR (400 MHz, DMSO-$d_6$): δ=7.87 (s, 1H), 6.70 (d, J=15.6 Hz, 1H), 6.89 (s, 1H), 6.59 (d, J=15.2 Hz, 1H), 2.78 (t, J=7.2 Hz, 4H), 2.67 (t, J=7.2 Hz, 4H), 2.49-2.50 (m, 2H), 2.28 (s, 3H), 1.98-1.90 (m, 4H), 1.19 (s, 6H), 1.01 (t, J=6.8 Hz, 3H); MS (TOF): m/z (%)=406.2131 (100%) $(M+H)^+$, 404.1986 (100%) (M−1).

Example-21

(E)-3-(cyclobutyl(methyl)amino)-N-((1,2,3,5,6,7-hexahydro-s-indacen-4-yl)carbamoyl)-3-methylbut-1-ene-1-sulfonamide

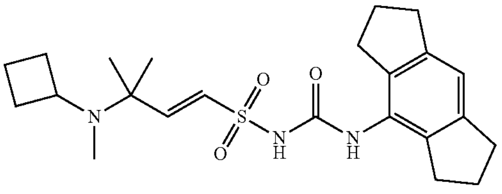 [SMILES: CN(C1CCC1)C(C)(C)/C=C/S(=O)(=O)NC(=O)Nc1c2c(cc3c1CCC3)CCC2]

$^1$H NMR (400 MHz, DMSO-$d_6$): δ=10.33 (brs, 1H), 7.97 (s, 1H), 6.97 (s, 1H), 6.77-6.58 (m, 2H), 3.52-3.37 (m, 1H), 2.79 (t, J=7.2 Hz, 4H), 2.67 (t, J=7.2 Hz, 4H), 2.81 (s, 3H), 1.99-1.87 (m, 8H), 1.59-1.40 (m, 2H), 1.15 (s, 6H); MS (TOF): m/z (%)=432.2295 (100%) $(M+H)^+$, 430.2140 (100%) (M−1).

Example-22

(E)-N-((1,2,3,5,6,7-hexahydro-s-indacen-4-yl)carbamoyl)-3-(methyl(tetrahydro-2H-thiopyran-4-yl)amino)prop-1-ene-1-sulfonamide

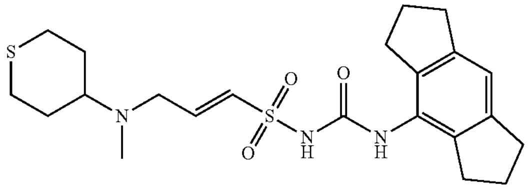 [SMILES: CN(C/C=C/S(=O)(=O)NC(=O)Nc1c2c(cc3c1CCC3)CCC2)C1CCSCC1]

$^1$H NMR (400 MHz, DMSO-$d_6$): δ=8.05 (s, 1H), 6.94 (s, 1H), 6.84 (d, J=15.2 Hz, 1H), 6.68 (dt, J=14.8 Hz, J=5.6 Hz, 1H), 3.33-3.31 (m, 2H), 2.80 (t, J=7.2 Hz, 4H), 2.67 (t, J=7.2 Hz, 4H), 2.61-2.52 (m, 5H), 2.20 (s, 1H), 2.00-1.91 (m, 6H), 1.61-1.50 (m, 2H); MS (TOF): m/z (%)=450.1869 (100%) $(M+H)^+$, 448.1711 (50%) (M−1).

Example-23

(E)-3-(cyclobutyl(methyl)amino)-N-((1,2,3,5,6,7-hexahydro-s-indacen-4-yl)carbamoyl)-3-methylbut-1-ene-1-sulfonamide

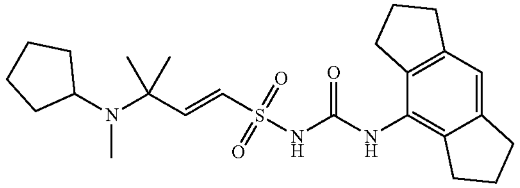 [SMILES: CN(C1CCCC1)C(C)(C)/C=C/S(=O)(=O)NC(=O)Nc1c2c(cc3c1CCC3)CCC2]

$^1$H NMR (400 MHz, DMSO-$d_6$): δ=8.21 (s, 1H), 6.93 (s, 1H), 6.71-6.86 (m, 2H), 3.64-3.61 (m, 1H), 2.80 (t, J=7.2 Hz, 4H), 2.68 (t, J=7.2 Hz, 4H), 2.33 (s, 3H), 1.99-1.91 (m, 4H), 1.72-1.60 (m, 2H), 1.59-1.45 (m, 4H), 1.41-1.10 (m, 8H); MS (TOF): m/z (%)=446.2457 (100%) $(M+H)^+$, 444.2307 (40%) (M−1).

Example-24

(E)-N-((1,2,3,5,6,7-hexahydro-s-indacen-4-yl)carbamoyl)-3-(isopropyl(methyl)amino)-3-methylbut-1-ene-1-sulfonamide

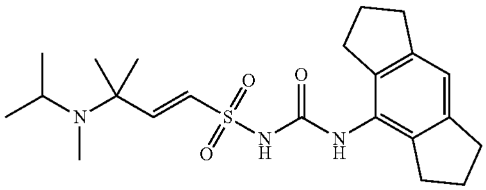 [SMILES: CC(C)N(C)C(C)(C)/C=C/S(=O)(=O)NC(=O)Nc1c2c(cc3c1CCC3)CCC2]

$^1$H NMR (400 MHz, DMSO-$d_6$): δ=7.94 (s, 1H), 6.92 (s, 1H), 6.75-6.59 (m, 2H), 3.34-3.21 (m, 1H), 2.80 (t, J=7.2 Hz, 4H), 2.67 (t, J=7.2 Hz, 4H), 2.20 (s, 3H), 1.99-1.92 (m,

8H), 1.22 (s, 6H), 0.98 (d, J=6.4 Hz, 6H); MS (TOF): m/z (%)=420.2871 (100%) $(M+H)^+$, 418.2452 (100%) (M−1).

Example-25

(E)-3-((cyclopropylmethyl)amino)-N-((1,2,3,5,6,7-hexahydro-s-indacen-4-yl)carbamoyl)-3-methylbut-1-ene-1-sulfonamide

[V]

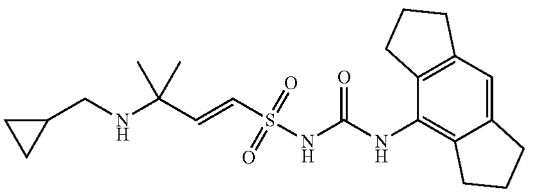

$^1$H NMR (400 MHz, DMSO-$d_6$): δ=7.49 (s, 1H), 6.81 (s, 1H), 6.77 (d, J=15.6 Hz, 1H), 6.38 (d, J=15.6 Hz, 1H), 2.77 (t, J=7.2 Hz, 4H), 2.70 (t, J=7.2 Hz, 4H), 2.65 (d, J=7.2 Hz, 2H), 1.96-1.89 (m, 4H), 1.34 (s, 6H), 0.97-0.89 (m, 1H), 0.54-0.48 (m, 2H), 0.30-0.22 (m, 2H); MS (TOF): m/z (%)=418.2132 (100%) $(M+H)^+$, 416.1982 (30%) (M−1).

Example-26

(E)-3-(cyclobutyl(methyl)amino)-N-((1,2,3,5,6,7-hexahydro-s-indacen-4-yl)carbamoyl)prop-1-ene-1-sulfonamide

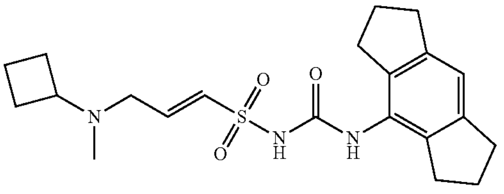 [SMILES: CN(C/C=C/S(=O)(=O)NC(=O)Nc1c2c(cc3c1CCC3)CCC2)C1CCC1]

$^1$H NMR (400 MHz, DMSO-$d_6$): δ=10.49 (brs, 1H), 8.02 (s, 1H), 6.93 (s, 1H), 6.85 (d, J=15.2 Hz, 1H), 6.69-6.63 (m, 1H), 3.14 (d, J=5.6 Hz, 2H), 2.99-2.91 (m, 1H), 2.80 (t, J=7.2 Hz, 4H), 2.67 (t, J=7.2 Hz, 4H), 2.09 (s, 3H), 2.01-1.90 (m, 8H), 1.85-1.75 (m, 2H), 1.65-1.51 (m, 2H); MS (TOF): m/z (%)=404.1974 (100%) $(M+H)^+$, 402.1866 (10%) (M−1).

Example-27

(E)-3-(dicyclobutylamino)-N-((1,2,3,5,6,7-hexahydro-s-indacen-4-yl)carbamoyl)prop-1-ene-1-sulfonamide

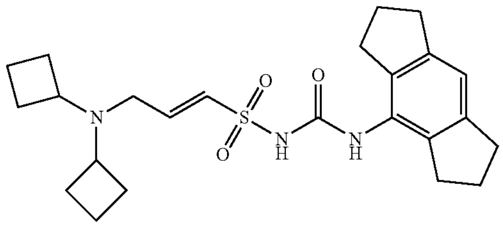 [SMILES: O=C(Nc1c2c(cc3c1CCC3)CCC2)NS(=O)(=O)/C=C/CN(C1CCC1)C1CCC1]

$^1$H NMR (400 MHz, DMSO-$d_6$): δ=10.31 (brs, 1H), 8.07 (s, 1H), 6.95 (s, 1H), 6.86 (d, J=15.2 Hz, 1H), 6.78-6.72 (m, 1H), 3.29-3.21 (m, 2H), 3.20-3.05 (m, 2H), 2.81 (t, J=7.2 Hz, 4H), 2.68 (t, J=7.2 Hz, 4H), 2.00-1.76 (m, 12H), 1.60-1.44 (m, 4H); MS (TOF): m/z (%)=444.2285 (100%) $(M+H)^+$, 442.2158 (30%) (M−1).

Example-28 tert-butyl (Z)-(3-(N-((1,2,3,5,6,7-hexahydro-s-indacen-4-yl)carbamoyl)sulfamoyl)allyl)carbamate

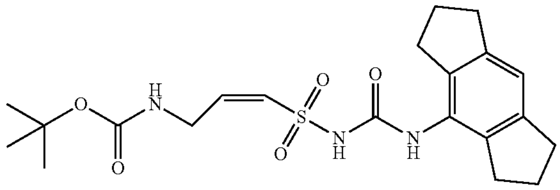 [SMILES: CC(C)(C)OC(=O)NC/C=C\S(=O)(=O)NC(=O)Nc1c2c(cc3c1CCC3)CCC2]

$^1$H NMR (400 MHz, DMSO-$d_6$): δ=10.52 (brs, 1H), 8.12 (s, 1H), 7.19-7.16 (m, 1H), 6.96 (s, 1H), 6.51 (dt, J=11.2 Hz, J=2.4 Hz, 1H), 6.30-6.23 (m, 1H), 4.10-4.09 (m, 2H), 2.81 (t, J=7.2 Hz, 4H), 2.71 (t, J=7.2 Hz, 4H), 2.01-1.91 (m, 4H), 1.38 (s, 9H); MS (TOF): m/z (%)=436.1961 (5%) $(M+H)^+$, 458.1747 (40%) (M+Na), 434.1802 (5%) (M−1).

Example-29

(Z)-3-amino-N-((1,2,3,5,6,7-hexahydro-s-indacen-4-yl)carbamoyl)prop-1-ene-1-sulfonamide 2,2,2-trifluoroacetate

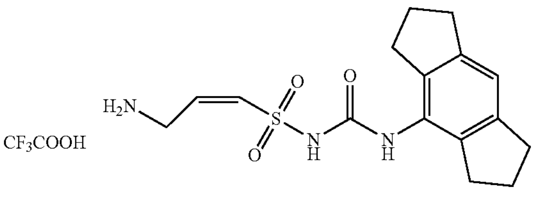 [SMILES: "CF3COOH" ; NC/C=C\S(=O)(=O)NC(=O)Nc1c2c(cc3c1CCC3)CCC2]

$^1$H NMR (400 MHz, DMSO-$d_6$): δ=10.96 (brs, 1H), 8.52 (s, 1H), 8.00 (s, 3H), 6.97 (s, 1H), 6.74 (d, J=11.2 Hz, 1H), 6.40-6.34 (m, 1H), 4.19-4.05 (m, 2H), 2.81 (t, J=7.2 Hz, 4H), 2.68 (t, J=7.2 Hz, 4H), 2.07-1.94 (m, 4H); MS (TOF): m/z (%)=336.1851 (100%) $(M+H)^+$, 334.1538 (30%) (M−1).

Example-30

(Z)-3-(dimethylamino)-N-((1,2,3,5,6,7-hexahydro-s-indacen-4-yl)carbamoyl)prop-1-ene-1-sulfonamide

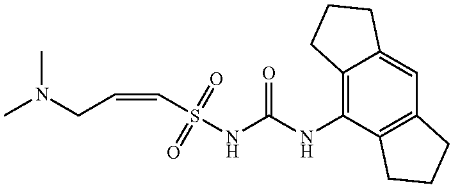 [SMILES: CN(C)C/C=C\S(=O)(=O)NC(=O)Nc1c2c(cc3c1CCC3)CCC2]

$^1$H NMR (400 MHz, DMSO-$d_6$): δ=11.21 (brs, 1H), 8.08 (s, 1H), 6.84 (s, 1H), 6.57 (d, J=11.2 Hz, 1H), 6.24-6.17 (m, 1H), 3.95 (d, J=7.6 Hz, 2H), 2.77 (t, J=7.2 Hz, 4H), 2.70-2.68 (m, 10H), 1.99-1.86 (m, 4H); MS (TOF): m/z (%)=364.2137 (100%) $(M+H)^+$, 362.1824 (10%) (M−1).

Example-31 sodium (E)-((3-(dimethylamino)-3-methylbut-1-en-1-yl)sulfonyl)((1,2,3,5,6,7-hexahydro-s-indacen-4-yl)carbamoyl)amide

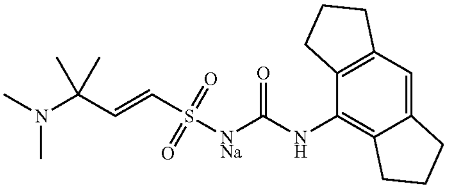

$^1$H NMR (400 MHz, DMSO-$d_6$): δ=7.36 (s, 1H), 6.77 (s, 1H), 6.51 (d, J=15.6 Hz, 1H), 6.23 (d, J=15.6 Hz, 1H), 2.76 (t, J=7.2 Hz, 4H), 2.69 (t, J=7.2 Hz, 4H), 2.11 (s, 1H), 1.94-1.87 (m, 4H), 1.06 (s, 6H); MS (TOF): m/z (%)=392.1987 (100%) $(M+H)^+$, 390.1841 (20%) (M−1).

Example-32 sodium (E)-((3-(dimethylamino)prop-1-en-1-yl) sulfonyl)((1,2,3,5,6,7-hexahydro-s-indacen-4-yl) carbamoyl)amide

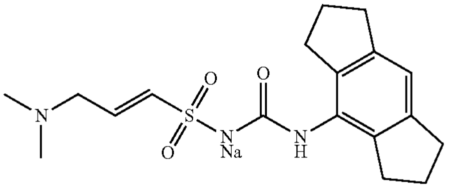

$^1$H NMR (400 MHz, DMSO-$d_6$): δ=7.36 (s, 1H), 6.77 (s, 1H), 6.62 (d, J=15.2 Hz, 1H), 6.18 (dt, J=15.2 Hz, J=6.4 Hz, 1H), 2.91 (dd, J=6.4 Hz, J=1.2 Hz, 2H), 2.76 (t, J=7.2 Hz, 4H), 2.69 (t, J=7.2 Hz, 4H), 2.13 (s, 6H), 1.96-1.70 (m, 4H); MS(TOF): m/z (%)=364.1676 (100%) $(M+H)^+$, 362.1552 (5%) (M−1).

Example-33

(E)-3-((3-aminopropyl)(methyl)amino)-N-((1,2,3,5,6,7-hexahydro-s-indacen-4-yl)carbamoyl)prop-1-ene-1-sulfonamide

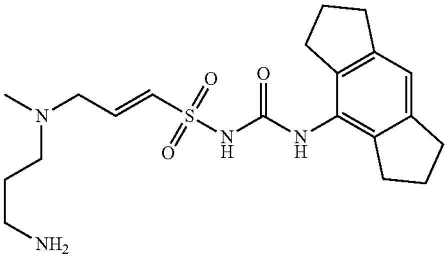 [SMILES: CN(C/C=C/S(=O)(=O)NC(=O)Nc1c2c(cc3c1CCC3)CCC2)CCCN]

$^1$H NMR (400 MHz, DMSO-$d_6$): δ=7.47 (s, 1H), 6.79 (s, 1H), 6.64 (d, J=15.2 Hz, 1H), 6.27-6.20 (m, 1H), 3.03 (d, J=6.0 Hz, 2H), 2.80-2.75 (m, 6H), 2.68 (t, J=7.2 Hz, 4H), 2.38 (t, J=6.4 Hz, 2H), 2.10 (s, 3H), 1.95-1.88 (m, 4H), 1.68-1.63 (m, 2H); MS (TOF): m/z (%)=407.2104 (100%) $(M+H)^+$, 405.2004 (10%) $(M-1)^-$.

Example-34

(E)-N-((1,2,3,5,6,7-hexahydro-s-indacen-4-yl)carbamoyl)-3-(piperidin-1-yl)prop-1-ene-1-sulfonamide

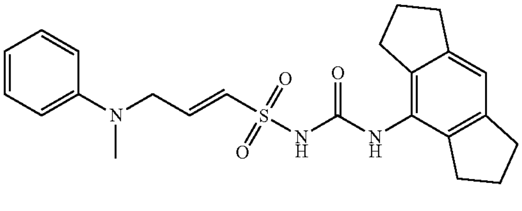 [SMILES: CN(C/C=C/S(=O)(=O)NC(=O)Nc1c2c(cc3c1CCC3)CCC2)c1ccccc1]

$^1$H NMR (400 MHz, DMSO-$d_6$): δ=8.02 (s, 1H), 7.15 (m, 3H), 6.95 (d, J=11.2 Hz, 2H), 6.65 (m, 6H), 6.47 (t, J=3.6 Hz, 1H), 4.18 (d, J=3.2 Hz, 2H), 2.91 (t, J=2.4 Hz, 4H), 2.79 (t, J=7.2 Hz, 4H), 2.65 (t, J=7.2 Hz, 4H), 1.983 (m, 4H); MS (ESI): m/z (%)=426.18 (100%) (M+1).

Example-35

(E)-N-((1,2,3,5,6,7-hexahydro-s-indacen-4-yl)carbamoyl)-3-(isobutyl(methyl)amino)-3-methylbut-1-ene-1-sulfonamide

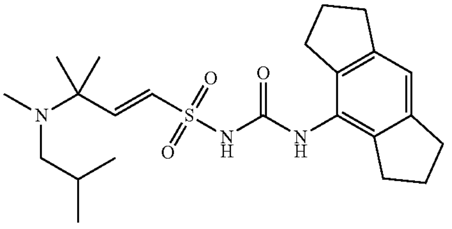 [SMILES: CC(C)CN(C)C(C)(C)/C=C/S(=O)(=O)NC(=O)Nc1c2c(cc3c1CCC3)CCC2]

$^1$H NMR (400 MHz, DMSO-$d_6$): δ=10.34 (brs, 1H), 8.04 (s, 1H), 6.94 (s, 1H), 6.72 (d, J=15.6 Hz, 1H), 6.66 (d, J=15.2 Hz, 1H), 2.80 (t, J=7.2 Hz, 4H), 2.67 (t, J=7.2 Hz, 4H), 2.14 (s, 3H), 2.10-2.08 (m, 2H), 2.00-1.92 (m, 4H), 1.68-1.61 (m, 1H), 1.13 (s, 6H), 0.82 (d, J=6.8 Hz, 3H); MS (TOF): m/z (%)=434.3021 (100%) $(M+H)^+$, 432.2628 (20%) (M−1).

Example-36

(E)-3-(dimethylamino)-N-((1,2,3,7-tetrahydro-s-indacen-4-yl)carbamoyl)prop-1-ene-1-sulfonamide

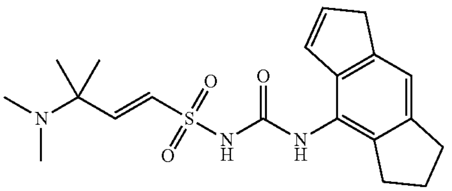 [SMILES: CN(C)C(C)(C)/C=C/S(=O)(=O)NC(=O)Nc1c2c(cc3c1CCC3)CC=C2]

$^1$H NMR (400 MHz, DMSO-$d_6$): δ=8.21 (bs, 1H), 7.16 (s, 1H), 6.87 (d, J=15.2 Hz, 1H), 6.80 (d, J=5.6 Hz, 1H), 6.69-6.51 (m, 1H), 6.40 (d, J=5.6 Hz, 1H), 3.30-3.28 (m, 4H), 2.87 (t, J=7.2 Hz, 2H), 2.74 (t, J=7.2 Hz, 2H), 2.32 (s, 6H), 2.02-1.95 (m, 2H); MS (TOF): m/z (%)=362.15 (100%) $(M+H)^+$.

Example-37

(E)-N-((1,2,3,5,6,7-hexahydro-s-indacen-4-yl)carbamoyl)-3-methyl-3-(methylsulfonamido)but-1-ene-1-sulfonamide

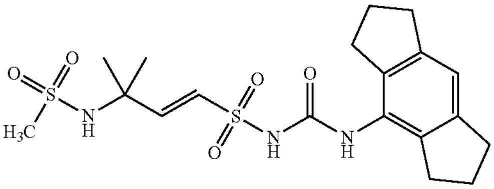 [SMILES: CC(C)(/C=C/S(=O)(=O)NC(=O)Nc1c2c(cc3c1CCC3)CCC2)NS(C)(=O)=O]

$^1$H NMR (400 MHz, DMSO-$d_6$): δ=10.47 (brs, 1H), 8.10 (s, 1H), 7.42 (s, 1H), 6.96 (s, 1H), 6.89 (d, J=15.2 Hz, 1H), 6.75 (d, J=15.2 Hz, 1H), 2.99 (s, 3H), 2.81 (t, J=7.2 Hz, 4H), 2.68 (t, J=7.2 Hz, 4H), 2.01-1.93 (m, 4H), 1.40 (s, 6H); MS (TOF): m/z (%)=442.1452 (100%) $(M+H)^+$, 440.1309 (20%) (M−1).

Example-38

(E)-3-(dimethylamino)-N-((1,2,3,5-tetrahydro-s-indacen-4-yl)carbamoyl)prop-1-ene-1-sulfonamide

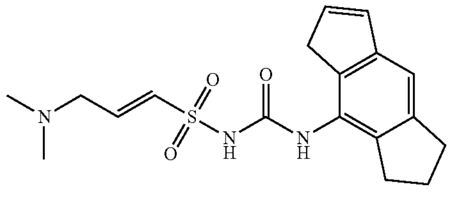 [SMILES: CN(C)C/C=C/S(=O)(=O)NC(=O)Nc1c2c(cc3c1CCC3)C=CC2]

$^1$H NMR (400 MHz, DMSO-$d_6$): δ=8.11 (bs, 1H), 7.10 (s, 1H), 6.88 (d, J=15.2 Hz, 1H), 6.83 (d, J=5.6 Hz, 1H), 6.61-6.52 (m, 1H), 6.50 (d, J=5.2 Hz, 1H), 3.32-3.26 (m, 4H), 2.87 (t, J=7.2 Hz, 2H), 2.76 (t, J=7.2 Hz, 2H), 2.34 (s, 6H), 2.03-1.95 (m, 2H); MS (TOF): m/z (%)=362.15 (100%) $(M+H)^+$.

Example-39

(E)-3-(dipropylamino)-N-((1,2,3,5,6,7-hexahydro-s-indacen-4-yl)carbamoyl)prop-1-ene-1-sulfonamide

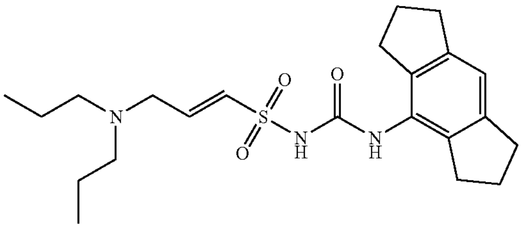 [SMILES: CCCN(C/C=C/S(=O)(=O)NC(=O)Nc1c2c(cc3c1CCC3)CCC2)CCC]

$^1$H NMR (400 MHz, DMSO-$d_6$): δ=7.96 (s, 1H), 6.92 (s, 1H), 3.32 (t, J=7.2 Hz, 4H), 2.80 (t, J=7.2 Hz, 4H), 2.70 (t, J=7.2 Hz, 4H), 2.63 (t, J=7.2 Hz, 2H), 2.50-2.45 (m, 2H), 2.00-1.91 (m, 4H), 1.86-1.82 (m, 2H), 1.46-1.40 (m, 4H), 0.84 (d, J=7.2 Hz, 6H); MS (TOF): m/z (%)=422.2451 (100%) $(M+H)^+$, 420.2326 (20%) (M−1).

Example-40

(E)-N-((1,2,3,5,6,7-hexahydro-s-indacen-4-yl)carbamoyl)-3-((2-methyl-2-(pyrrolidin-1-yl)propyl)amino)prop-1-ene-1-sulfonamide

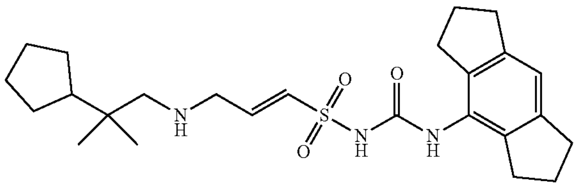 [SMILES: CC(C)(CNC/C=C/S(=O)(=O)NC(=O)Nc1c2c(cc3c1CCC3)CCC2)C1CCCC1]

$^1H$ NMR (400 MHz, DMSO-$d_6$): δ=7.48 (s, 1H), 6.77 (s, 1H), 6.69 (d, J=15.2 Hz, 1H), 6.27-6.22 (m, 1H), 3.25-3.24 (m, 2H), 2.76 (t, J=7.2 Hz, 4H), 2.70 (t, J=7.2 Hz, 4H), 2.64-2.60 (m, 4H), 2.45 (s, 2H), 1.95-1.89 (m, 4H), 1.67-1.65 (m, 4H), 1.01 (s, 6H); MS (TOF): m/z (%)=461.2562 (100%) $(M+H)^+$, 459.2421 (30%) $(M-1)^-$.

Example-41

(E)-N-((1,2,3,5,6,7-hexahydro-s-indacen-4-yl)carbamoyl)-3-(methyl(2-methyl-2-(pyrrolidin-1-yl)propyl)amino)prop-1-ene-1-sulfonamide

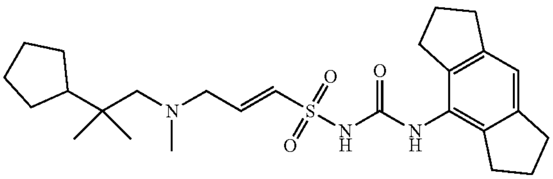 [SMILES: CN(C/C=C/S(=O)(=O)NC(=O)Nc1c2c(cc3c1CCC3)CCC2)CC(C)(C)C1CCCC1]

$^1H$ NMR (400 MHz, DMSO-$d_6$): δ=7.48 (s, 1H), 6.77 (s, 1H), 6.69 (d, J=15.2 Hz, 1H), 6.27-6.22 (m, 1H), 3.25-3.24 (m, 2H), 2.76 (t, J=7.2 Hz, 4H), 2.70 (t, J=7.2 Hz, 4H), 2.64-2.60 (m, 4H), 2.45 (s, 2H), 2.19 (s, 3H), 1.95-1.89 (m, 4H), 1.67-1.65 (m, 4H), 1.01 (s, 6H); MS (TOF): m/z (%)=475.2717 (100%) $(M+H)^+$, 473.2633 (30%) $(M-1)^-$.

Example-42

(E)-N-((1,2,3,5,6,7-hexahydro-s-indacen-4-yl)carbamoyl)-3-methyl-3-(pyrrolidin-1-yl)but-1-ene-1-sulfonamide

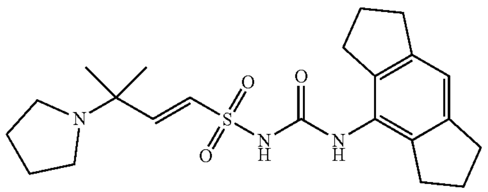 [SMILES: CC(C)(/C=C/S(=O)(=O)NC(=O)Nc1c2c(cc3c1CCC3)CCC2)N1CCCC1]

$^1H$ NMR (400 MHz, DMSO-$d_6$): δ=7.79 (s, 1H), 6.87 (s, 1H), 6.76 (d, J=15.6 Hz, 1H), 6.61 (d, J=15.6 Hz, 1H), 2.78 (t, J=7.2 Hz, 8H), 2.68 (t, J=7.2 Hz, 4H), 1.96 (t, J=7.2 Hz, 4H), 1.71 (br s, 4H), 1.28 (s, 6H); MS (TOF): m/z (%)=418.2295 (100%) $(M+H)^+$.

Example-43

(E)-4-(dimethylamino)-N-((1,2,3,5,6,7-hexahydro-s-indacen-4-yl)carbamoyl)but-1-ene-1-sulfonamide

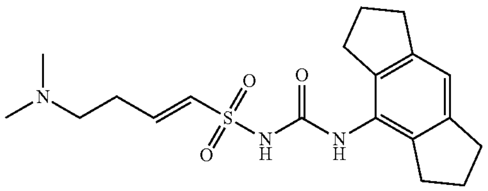 [SMILES: CN(C)CC/C=C/S(=O)(=O)NC(=O)Nc1c2c(cc3c1CCC3)CCC2]

$^1H$ NMR (400 MHz, DMSO-$d_6$): δ=7.85 (s, 1H), 6.90 (s, 1H), 6.74 (d, J=15.2 Hz, 1H), 6.58-6.51 (m, 1H), 2.79 (t, J=7.2 Hz, 2H), 2.72-2.65 (m, 6H), 2.46-2.43 (m, 2H), 2.30 (s, 6H), 1.97-1.91 (m, 4H); MS (TOF): m/z (%)=378.1834 (100%) $(M+H)^+$, 376.1680 (100%) $(M-1)^-$;

Example-44

(E)-4-amino-N-((1,2,3,5,6,7-hexahydro-s-indacen-4-yl)carbamoyl)but-1-ene-1-sulfonamide

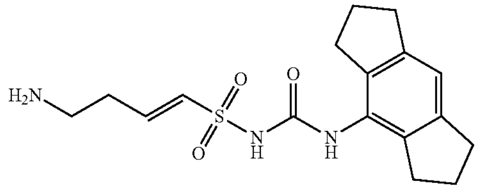 [SMILES: NCC/C=C/S(=O)(=O)NC(=O)Nc1c2c(cc3c1CCC3)CCC2]

$^1H$ NMR (400 MHz, DMSO-$d_6$): δ=7.46 (s, 1H), 6.79 (s, 1H), 6.58 (d, J=15.2 Hz, 1H), 6.26-6.19 (m, 1H), 2.88 (t, J=7.2 Hz, 2H), 2.76 (t, J=7.2 Hz, 4H), 2.69 (t, J=7.2 Hz, 4H), 2.40-2.33 (m, 2H), 1.96-1.89 (m, 4H); MS (TOF): m/z (%)=350.1945 (100%) $(M+H)^+$, 348.1652 (10%) $(M-1)^-$.

Example 45 tert-butyl (E)-(3-(N-((1,2,3,5,6,7-hexahydro-s-indacen-4-yl)carbamoyl)sulfamoyl)allyl)carbamate

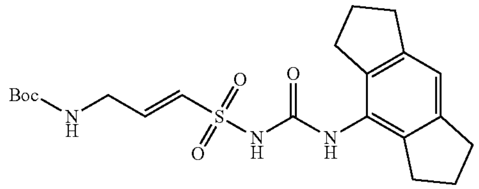 [SMILES: CC(C)(C)OC(=O)NC/C=C/S(=O)(=O)NC(=O)Nc1c2c(cc3c1CCC3)CCC2]

1H NMR (400 MHz, DMSO-d6): δ=10.49 (br s, 1H), 8.09 (s, 1H), 7.28 (t, J=5.6 Hz, 1H), 6.96 (s, 1H), 6.78-6.72 (m, 1H), 6.67 (d, J=15.6 Hz, 1H), 3.96-3.85 (m, 2H), 2.81 (t, J=7.2 Hz, 4H), 2.01 (t, J=7.2 Hz, 4H), 2.01-1.94 (m, 4H), 1.42 (s, 9H).

Scheme 2

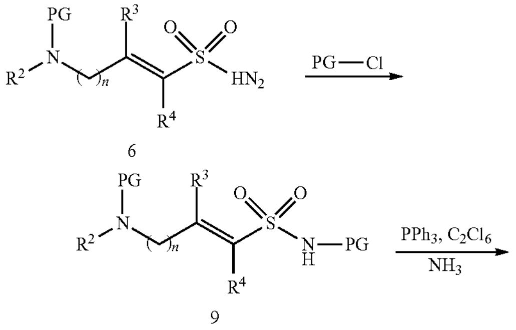

-continued

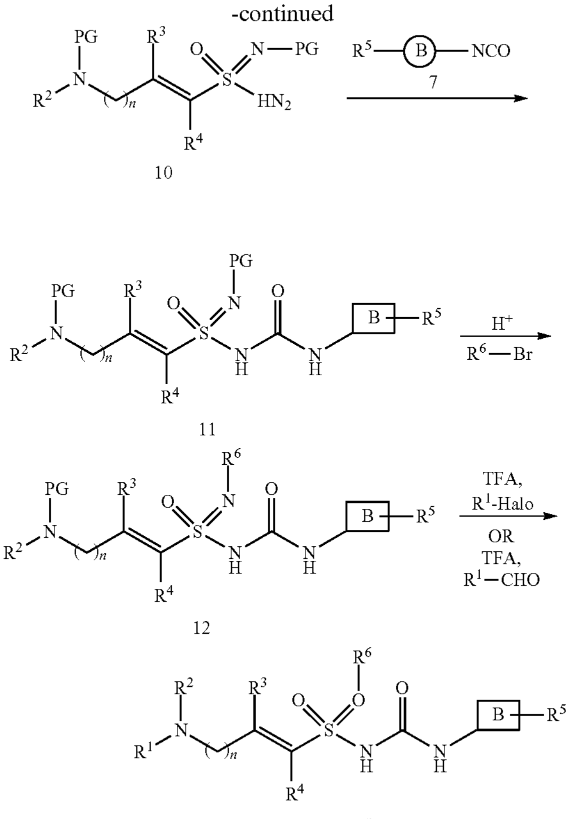

10

11

12

Formula (I'')

Wherein each of 'A', $R^1$, $R^2$, $R^3$, $R^4$ and $R^5$ are as defined earlier. Synthesis of Compound 6 is described earlier. Protection of amine group of 6 with suitable protecting groups like substituted silyl chlorides afforded 9. Compound 9 on treatment with triphenyl phosphine and hexachloroethane followed by ammonia, under suitable conditions and appropriate solvents provide compound 10. Compound 10 on treatment with isocyanato derivative (7) under suitable conditions, base like butyl lithium or sodium hydrate and appropriate solvents yielded 11. Compound 11 was subjected to the deprotection with suitable reagent under suitable conditions, followed by reaction with alkyl bromide to provide 12. Deprotection of compound 12 followed by treatment with alkyl bromide or aldehyde or ketone derivative under suitable conditions in presence of base like sodium hydride and appropriate solvent, under suitable conditions to afford compound of Formula (I'').

Specific reaction conditions, solvents and other parameters necessary for carrying out the process steps as described above are well within the capabilities of a person skilled in the art.

The invention is further illustrated by the following non-limiting examples which describe the preferred way of carrying out the present invention. These are provided without limiting the scope of the present invention in any way.

$^1$H NMR spectral data given in the examples (vide infra) are recorded using a 400 MHz spectrometer (Bruker AVANCE-400) and reported in δ scale. Until and otherwise mentioned the solvent used for NMR is $CDCl_3$ using TMS as the internal standard.

Example-49

Preparation of (E)-N'-cyano-3-(dimethylamino)-N-((1,2,3,5,6,7-hexahydro-s-indacen-4-yl)carbamoyl)-3-methylbut-1-ene-1-sulfonimidamide

Intermediate-5: Preparation of tert-butyl (E)-(4-(N-(tert-butyldiphenylsilyl)sulfamoyl)-2-methylbut-3-en-2-yl)carbamate

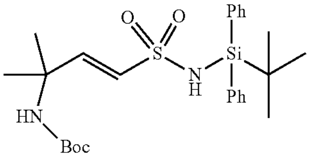 [SMILES: CC(C)(/C=C/S(=O)(=O)N[Si](c1ccccc1)(c1ccccc1)C(C)(C)C)NC(=O)OC(C)(C)C]

To a solution of tert-butyl (E)-(2-methyl-4-sulfamoylbut-3-en-2-yl)carbamate (5 g, 18.92 mmol) in THF (50 ml) was added triethylamine (6.59 ml, 47.3 mmol) at room temperature. The reaction mixture was stirred at 50° C. for 0.5 h. TBDPS-Cl (6.07 ml, 23.64 mmol) was added dropwise at 50° C. The reaction mixture was stirred at 50° C. for 16 h. Further triethylamine (6.59 ml, 47.3 mmol) and TBDPS-Cl (6.07 ml, 23.64 mmol) were added at 50° C. The reaction mixture was stirred at 50° C. for 16 h. The reaction mixture was evaporated to get crude product. The crude product was purified by column chromatography using EtOAc: hexane as eluent to afford tert-butyl (E)-(4-(N-(tert-butyldiphenylsilyl) sulfamoyl)-2-methylbut-3-en-2-yl)carbamate (4 g, 7.96 mmol, 42.1% yield)

$^1$H NMR (400 MHz, DMSO-$d_6$): δ=7.77-7.70 (m, 5H), 7.48-7.40 (m, 6H), 6.97 (bs, 1H), 6.97 (d, J=14.8 Hz, 1H), 6.14 (d, J=15.2 Hz, 1H), 1.38 (s, 9H), 1.24 (s, 6H), 0.95 (s, 9H); MS (TOF): m/z (%)=525.22 (20%) (M+Na)+

Intermediate-6: Preparation of tert-butyl (E)-(4-(N-(tert-butyldiphenylsilyl)sulfamidimidoyl)-2-methylbut-3-en-2-yl)carbamate

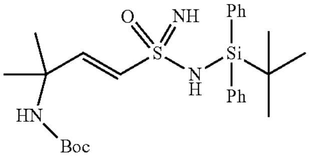 [SMILES: CC(C)(/C=C/S(=N)(=O)N[Si](c1ccccc1)(c1ccccc1)C(C)(C)C)NC(=O)OC(C)(C)C]

A solution of triphenylphosphine (0.678 g, 2.59 mmol) and perchloroethane (0.612 g, 2.59 mmol) in dry Chloroform (10 mL) was heated to 70° C. for 6 h under nitrogen atmosphere. Solid ppt was cooled to room temperature and added triethylamine (0.491 ml, 3.52 mmol), stirred for 10 min. and cooled to 0° C. and added a solution of tert-butyl (E)-(4-(N-(tert-butyldiphenylsilyl)sulfamoyl)-2-methylbut-3-en-2-yl)carbamate (1 g, 1.989 mmol) in CHCl3 (10 mL), it was stirred for 30 min at 0° C. and ammonia gas was purged at 0° C. for 1 h. The solvent was evaporated to get crude product. Crude product was purified by column chromatography using EtOAc: hexane as eluent phase to afford tert-butyl (E)-(4-(N-(tert-butyldiphenylsilyl)sulfamidimidoyl)-2-methylbut-3-en-2-yl)carbamate (0.9 g, 1.794 mmol, 90% yield).

$^1$H NMR (400 MHz, DMSO-$d_6$): δ=7.76-7.73 (m, 4H), 7.38-7.31 (m, 6H), 6.86 (bs, 1H), 6.51 (s, 2H), 6.62 (d, J=14.8 Hz, 1H), 6.34 (d, J=15.2 Hz, 1H), 1.40 (s, 9H), 1.26-1.18 (m, 6H), 1.04 (s, 9H); MS (TOF): m/z (%)=502.24 (100%) (M+H)+.

Intermediate-7: Preparation of tert-butyl (E)-(4-(N'-(tert-butyldiphenylsilyl)-N-((1,2,3,5,6,7-hexahydro-s-indacen-4-yl)carbamoyl)sulfamidimidoyl)-2-methylbut-3-en-2-yl)carbamate

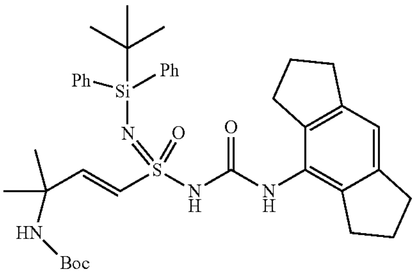 [SMILES: CC(C)(/C=C/S(=O)(=N[Si](c1ccccc1)(c1ccccc1)C(C)(C)C)NC(=O)Nc1c2c(cc3c1CCC3)CCC2)NC(=O)OC(C)(C)C]

To a solution of tert-butyl(E)-(4-(N-(tert-butyldiphenylsilyl)sulfamidimidoyl)-2-methylbut-3-en-2-yl)carbamate (0.4 g, 0.797 mmol) in THF (4 ml) was added NaH (0.070 g, 1.754 mmol) at 0° C. under nitrogen atmosphere. The reaction mixture was stirred further for 30 min. and further at room temperature for another 30 min. Solution of 4-isocyanato-1,2,3,5,6,7-hexahydro-s-indacene (0.191 g, 0.957 mmol) in THF was added in one portion. The resulted suspension was stirred further for 2 h at room temperature. The reaction mixture was acidified with 30% citric acid solution and water was added. The aqueous layer was extracted with ethyl acetate. The combined organic layers was dried over $Na_2SO_4$, the solvent was evaporated and residue purified by column chromatography using EtOAc: hexane to afford tert-butyl (E)-(4-(N'-(tert-butyldiphenylsilyl)-N-((1,2,3,5,6,7-hexahydro-s-indacen-4-yl)carbamoyl) sulfamidimidoyl)-2-methylbut-3-en-2-yl)carbamate (0.335 g, 0.478 mmol, 60% yield).

1H NMR (400 MHz, DMSO-d6): δ=9.78 (s, 1H), 8.00 (s, 1H), 7.75-7.74 (m, 4H), 7.39-7.34 (m, 6H), 6.96-6.93 (m, 2H), 6.84 (d, J=14.8 Hz, 1H), 6.64 (d, J=15.2 Hz, 1H) 2.79 (t, J=7.2 Hz, 4H), 2.62 (t, J=7.2 Hz, 4H), 1.99-1.91 (m, 4H), 1.41 (s, 9H), 1.26 (s, 6H), 1.04 (s, 9H); MS (ESI): m/z (%)=701.35 (100%) (M+H)+.

Intermediate-8 Preparation of tert-butyl (E)-(4-(N-((1,2,3,5,6,7-hexahydro-s-indacen-4-yl)carbamoyl) sulfamidimidoyl)-2-methylbut-3-en-2-yl)carbamate

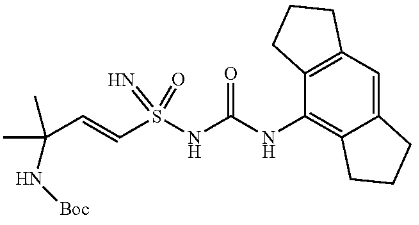 [SMILES: CC(C)(/C=C/S(=N)(=O)NC(=O)Nc1c2c(cc3c1CCC3)CCC2)NC(=O)OC(C)(C)C]

A solution of tert-butyl (E)-(4-(N'-(tert-butyldiphenylsilyl)-N-((1,2,3,5,6,7-hexahydro-s-indacen-4-yl)carbamoyl) sulfamidimidoyl)-2-methylbut-3-en-2-yl)carbamate (3.4 g, 4.85 mmol) in isopropyl acetate (34 ml) was added citric acid (19.40 ml, 48.5 mmol). The reaction mixture was stirred at room temperature for 48 h. The reaction mixture was concentrated under reduced pressure and solid product was filtered to get crude product. Crude product was purified by column chromatography using using EtOAc: hexane to afford tert-butyl(E)-(4-(N-((1,2,3,5,6,7-hexahydro-s-indacen-4-yl)carbamoyl)sulfamidimidoyl)-2-methylbut-3-en-2-yl)carbamate (1.2 g, 2.59 mmol, 53.5% yield).

$^1$H NMR (400 MHz, DMSO-$d_6$): δ=8.29 (bs, 1H), 7.19 (s, 1H), 7.00 (bs, 1H), 6.87 (s, 1H), 6.73 (d, J=16.0 Hz, 1H), 6.60 (d, J=15.2 Hz, 1H), 2.78 (t, J=7.2 Hz, 4H), 2.71 (t, J=7.2 Hz, 4H), 1.99-1.90 (m, 4H), 1.38 (s, 9H), 1.32 (s, 6H); MS (TOF): m/z (%)=463.29 (100%) (M+H)+.

Intermediate-9: Preparation of tert-butyl (E)-(4-(N'-cyano-N-((1,2,3,5,6,7-hexahydro-s-indacen-4-yl) carbamoyl)sulfamidimidoyl)-2-methylbut-3-en-2-yl) carbamate

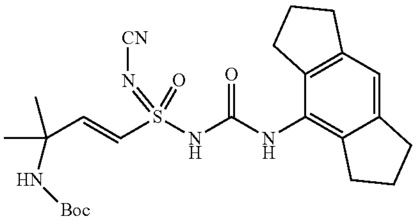 [SMILES: CC(C)(/C=C/S(=O)(=NC#N)NC(=O)Nc1c2c(cc3c1CCC3)CCC2)NC(=O)OC(C)(C)C]

To a solution of tert-butyl(E)-(4-(N-((1,2,3,5,6,7-hexahydro-s-indacen-4-yl)carbamoyl)sulfamidimidoyl)-2-methylbut-3-en-2-yl)carbamate (0.180 g, 0.389 mmol) in DMF (4 ml) was added triethylamine (0.217 ml, 1.556 mmol) and cyanic bromide (0.082 g, 0.778 mmol) at room temperature and the reaction mixture was stirred for 17 h at room temperature. The reaction mixture was purified by preparative HPLC to afford tert-butyl(E)-(4-(N'-cyano-N-((1,2,3,5,6,7-hexahydro-s-indacen-4y1)carbamoyl)sulfamidimidoyl)-2-methylbut-3-en-2-yl)carbamate (0.080 g, 0.164 mmol, 42.2% yield)

$^1$H NMR (400 MHz, DMSO-$d_6$): δ=7.86 (bs, 1H), 6.90 (bs, 1H), 6.83 (s, 1H), 6.65 (d, J=15.6 Hz, 1H), 6.47 (d, J=15.2 Hz, 1H), 2.77 (t, J=7.2 Hz, 4H), 2.71 (t, J=7.2 Hz, 4H), 1.96-1.88 (m, 4H), 1.37 (s, 9H), 1.30 (s, 6H); MS (TOF): m/z (%)=488.23 (100%) (M+H)+.

Intermediate-10: Preparation of (E)-3-amino-N'-cyano-N-((1,2,3,5,6,7-hexahydro-s-indacen-4-yl) carbamoyl)-3-methylbut-1-ene-1-sulfonimidamide

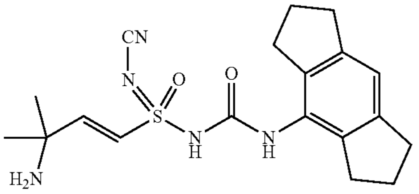 [SMILES: CC(C)(N)/C=C/S(=O)(=NC#N)NC(=O)Nc1c2c(cc3c1CCC3)CCC2]

A mixture of tert-butyl(E)-(4-(N'-cyano-N-((1,2,3,5,6,7-hexahydro-s-indacen-4yl)carbamoyl)sulfamidimidoyl)-2-methylbut-3-en-2-yl)carbamate (0.55 g, 1.128 mmol) and HCl in dioxane (3.76 ml, 11.28 mmol, 4M) was stirred for 1 h at room temperature. The solvent was evaporated to get crude product. Crude product was purified by Preparative HPLC to afford (E)-3-amino-N'-cyano-N-((1,2,3,5,6,7-hexahydro-s-indacen-4-yl)carbamoyl)-3-methylbut-1-ene-1-sulfonimidamide (0.095 g, 0.245 mmol, 21.74% yield).

$^1$H NMR (400 MHz, DMSO-$d_6$): δ=7.93 (bs, 1H), 6.84-6.80 (m, 2H), 6.56 (d, J=15.2 Hz, 1H), 2.77 (t, J=7.2 Hz, 4H), 2.71 (t, J=7.2 Hz, 4H), 1.95-1.88 (m, 4H), 1.34 (s, 6H); MS (TOF): m/z (%)=388.17 (100%) (M+H)+.

Example-49

(E)-N'-cyano-3-(dimethylamino)-N-((1,2,3,5,6,7-hexahydro-s-indacen-4-yl)carbamoyl)-3-methylbut-1-ene-1-sulfonimidamide

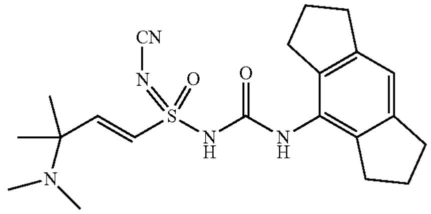 [SMILES: CN(C)C(C)(C)/C=C/S(=O)(=NC#N)NC(=O)Nc1c2c(cc3c1CCC3)CCC2]

To a solution of (E)-3-amino-N'-cyano-N-((1,2,3,5,6,7-hexahydro-s-indacen-4-yl)carbamoyl)-3-methylbut-1-ene-1-sulfonimidamide (0.085 g, 0.219 mmol) in MeOH (2 ml) was added triethyl amine (0.037 ml, 0.263 mmol), paraformaldehyde (0.023 g, 0.768 mmol) and sodium cyanotrihydroborate (0.034 g, 0.548 mmol) at room temperature. The reaction mixture was stirred at room temperature for 16 h. The solvent was evaporated and the crude product obtained was purified by preparative HPLC to afford (E)-N'-cyano-3-(dimethylamino)-N-((1,2,3,5,6,7-hexahydro-s-indacen-4-yl)carbamoyl)-3-methylbut-1-ene-1-sulfonimidamide (0.042 g, 0.101 mmol, 46.1% yield).

$^1$H NMR (400 MHz, DMSO-$d_6$): δ=9.70 (bs, 1H), 8.07 (bs, 1H), 6.90 (d, J=15.2 Hz, 1H), 6.83 (s, 1H), 6.52 (d, J=15.6 Hz, 1H), 2.78-2.75 (m, 10H), 2.69 (t, J=7.2 Hz, 4H), 1.98-1.88 (m, 4H), 1.45 (s, 6H); MS (TOF): m/z (%)=416.21 (100%) (M+H)+.

Using appropriate starting materials and suitable modifications of the process described in example 1, including suitable addition and/or deletion of steps as may be necessary which are well within the scope of a person skilled in the art, the following compounds were prepared in an analogues manner.

Example-46 tert-butyl (E)-(4-(N-((1,2,3,5,6,7-hexahydro-s-indacen-4-yl)carbamoyl)sulfamidimidoyl)-2-methylbut-3-en-2-yl)carbamate

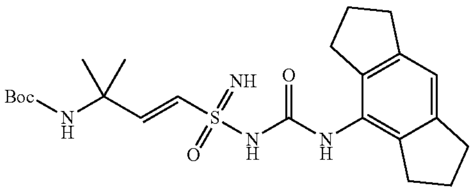 [SMILES: CC(C)(/C=C/S(=N)(=O)NC(=O)Nc1c2c(cc3c1CCC3)CCC2)NC(=O)OC(C)(C)C]

$^1$H NMR (400 MHz, DMSO-$d_6$): δ=8.29 (bs, 1H), 7.19 (s, 1H), 7.00 (bs, 1H), 6.87 (s, 1H), 6.73 (d, J=16.0 Hz, 1H), 6.60 (d, J=15.2 Hz, 1H), 2.78 (t, J=7.2 Hz, 4H), 2.71 (t, J=7.2 Hz, 4H), 1.99-1.90 (m, 4H), 1.38 (s, 9H), 1.32 (s, 6H); MS (TOF): m/z (%)=463.29 (100%) $(M+H)^+$.

Example-47 tert-butyl (E)-(4-(N'-cyano-N-((1,2,3,5,6,7-hexahydro-s-indacen-4-yl)carbamoyl)sulfamidimidoyl)-2-methylbut-3-en-2-yl)carbamate

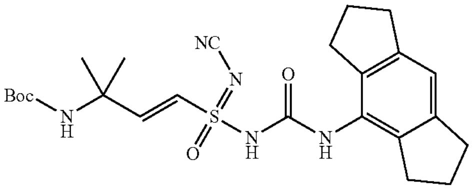 [SMILES: CC(C)(/C=C/S(=O)(=NC#N)NC(=O)Nc1c2c(cc3c1CCC3)CCC2)NC(=O)OC(C)(C)C]

$^1$H NMR (400 MHz, DMSO-$d_6$): δ=7.86 (bs, 1H), 6.90 (bs, 1H), 6.83 (s, 1H), 6.65 (d, J=15.6 Hz, 1H), 6.47 (d, J=15.2 Hz, 1H), 2.77 (t, J=7.2 Hz, 4H), 2.71 (t, J=7.2 Hz, 4H), 1.96-1.88 (m, 4H), 1.37 (s, 9H), 1.30 (s, 6H); MS (TOF): m/z (%)=488.23 (100%) $(M+H)^+$.

Example-48

(E)-3-amino-N'-cyano-N-((1,2,3,5,6,7-hexahydro-s-indacen-4-yl)carbamoyl)-3-methylbut-1-ene-1-sulfonimidamide

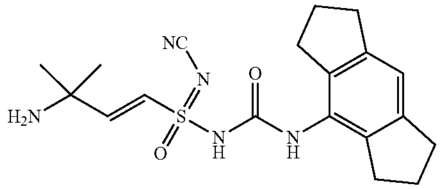 [SMILES: CC(C)(N)/C=C/S(=O)(=NC#N)NC(=O)Nc1c2c(cc3c1CCC3)CCC2]

$^1$H NMR (400 MHz, DMSO-$d_6$): δ=7.93 (bs, 1H), 6.84-6.80 (m, 2H), 6.56 (d, J=15.2 Hz, 1H), 2.77 (t, J=7.2 Hz, 4H), 2.71 (t, J=7.2 Hz, 4H), 1.95-1.88 (m, 4H), 1.34 (s, 6H); MS (TOF): m/z (%)=388.17 (100%) $(M+H)^+$.

Example-49

(E)-N'-cyano-3-(dimethylamino)-N-((1,2,3,5,6,7-hexahydro-s-indacen-4-yl)carbamoyl)-3-methylbut-1-ene-1-sulfonimidamide

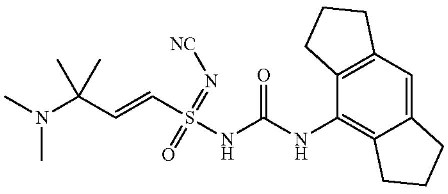 [SMILES: CN(C)C(C)(C)/C=C/S(=O)(=NC#N)NC(=O)Nc1c2c(cc3c1CCC3)CCC2]

$^1H$ NMR (400 MHz, DMSO-$d_6$): δ=9.70 (bs, 1H), 8.07 (bs, 1H), 6.90 (d, J=15.2 Hz, 1H), 6.83 (s, 1H), 6.52 (d, J=15.6 Hz, 1H), 2.78-2.75 (m, 10H), 2.69 (t, J=7.2 Hz, 4H), 1.98-1.88 (m, 4H), 1.45 (s, 6H); MS (TOF): m/z (%)=416.21 (100%) $(M+H)^+$.

Example-50

(E)-3-amino-N-((1,2,3,5,6,7-hexahydro-s-indacen-4-yl)carbamoyl)-3-methylbut-1-ene-1-sulfonimidamide

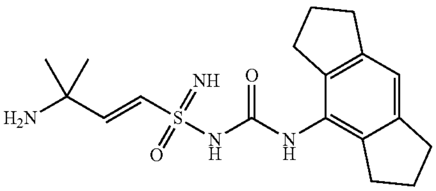 [SMILES: CC(C)(N)/C=C/S(=N)(=O)NC(=O)Nc1c2c(cc3c1CCC3)CCC2]

$^1H$ NMR (400 MHz, DMSO-$d_6$): δ=8.28 (bs, 1H), 6.87 (s, 1H), 6.72-6.64 (m, 2H), 2.78 (t, J=7.2 Hz, 4H), 2.71 (t, J=7.2 Hz, 4H), 1.97-1.90 (m, 4H), 1.30 (s, 6H); MS (TOF): m/z (%)=363.18 (100%) $(M+H)^+$.

Biological Activity:

In-Vitro Assays:

THP1 monocytes were differentiated with PMA (100 ng/ml) and incubated at 37° C. for 20 hrs in presence of 5% CO2. $2\times10^5$ differentiated cells were plated per well of 96 well tissue culture plates. The cells were primed using 500 ng/ml Lipopolysaccharide and incubating for 4 h under the same condition. The cells were then treated with various concentrations of the compounds for 30 min followed by treatment with 5 mM ATP for 1 hr. The supernatants were collected and analyzed by IL-1b (Mabtech Cat #3415-1H-20) or TNF-a (Mabtech; Cat #3510-1H-20) detection kit. The data were analyzed using GraphPad Prism V7.0. Dose Response Curve (DRC) was constructed to determine the $IC_{50}$ value by fitting percentage cell survival data to the GraphPad Prism using nonlinear regression analysis. The invitro IL-1β inhibitory activity ($IC_{50}$) for representative compounds are listed in Table 1.

TABLE 1

| Compound | $IC_{50}$ (nM) |
|---|---|
| Example 1 | 43 |
| Example 2 | 3.2 |
| Example 5 | 20 |
| Example 6 | 5.6 |
| Example 18 | 6.6 |
| Example 20 | 9.9 |
| Example 21 | 6.0 |
| Example 24 | 7.5 |
| Example 35 | 11 |
| Example 36 | 9.6 |
| Example 38 | 3.6 |
| Example 42 | 12.6 |
| Example 47 | 3.8 |
| Example 48 | 12 |
| Example 49 | 6.5 |

In Vivo Efficacy Studies:

Demonstration of in vivo efficacy of test compounds in rats mice, oral routes of administration.

Animals

All the animal experiments were carried out in female rats and mice, bred in-house. Animals were housed in groups of 6 animals per cage, for a week, in order to habituate them to vivarium conditions (25±4° C., 60-65% relative humidity, 12:12 h light: dark cycle, with lights on at 7.30 am). All the animal experiments were carried out according to the internationally valid guidelines following approval by the 'Zydus Research Center animal ethical committee'.

In-Vivo LPS and ATP Induced IL-1β Assay:

Female C57 mice (6-8 weeks) received intraperitoneal injection of 50 μg/mouse of lipopolysaccharide (LPS) in PBS. Animals were treated immediately with the test compounds or the vehicle. After 2 h of LPS injection, animals were administered with ATP at 12.5 mg/mouse dissolved in PBS via intraperitoneal route. After 30 minutes of ATP injection, serum was collected for IL-1β estimation by ELISA.

The novel compounds of the present invention can be formulated into suitable pharmaceutically acceptable compositions by combining with suitable excipients by techniques and processes and concentrations as are well known.

The compounds of formula (I) or pharmaceutical compositions containing them are useful as a medicament for the inhibition of NLRP3 activity and suitable for humans and other warm blooded animals, and may be administered either by oral, topical or parenteral administration.

Thus, a pharmaceutical composition comprising the compounds of the present invention may comprise a suitable binder, suitable bulking agent &/or diluent and any other suitable agents as may be necessary. Optionally, the pharmaceutical composition may be suitably coated with suitable coating agents.

The compounds of the present invention (I) are NLRP3 inhibitors and are useful in the treatment of disease states mediated by NLRP3, preferably diseases or conditions in which interleukin 1 β activity is implicated and related disorders.

The quantity of active component, that is, the compounds of Formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

The compounds of the present invention, formula (I), may be used alone or in any combination with one or more other therapeutic agents which a skilled medical practitioner can easily identify. Such other therapeutic agent may be selected depending on the type of disease being treated, the severity, other medications being taken by the patients etc. Thus for example, for treatment of rheumatoid arthritis, one or more DMARDs may be used in combination with the compounds of the present invention.

In one of the embodiments compound of formula (I) of the present invention may be used in combination with one or more suitable pharmaceutically active agents selected from following therapeutic agents in any combination. Inhibitors of interleukin-1β (e.g. rilonacept, canakinumab, and anakinra); immune-suppressants (e.g., Methotrexate, mercaptopurine, cyclophosphamide), metabolic disorders drugs, glucocorticoids, non-steroidal anti-inflammatory drugs, Cox-2 specific inhibitors, TNF-α binding proteins (eg., Infliximab, etanercept), interferon-13, interferon, interleukin-2, antihistamines, beta-agonist, BTK inhibitors, anticolinergics, anti-cancer agents or their suitable pharmaceutically acceptable salts. Further examples for use in combination with Non-Alcoholic Steato-Hepatitis (NASH) and fibrosis drugs, anticancer antibiotics, hormones, Aromatase inhibitors, antibodies, cytokines, vaccines, drug conjugates, inhibitors of mitogen-activated protein kinase signaling (ex: BAY 43-9006), Syk inhibitors, mTOR inhibitors, antibodies (Rituxan), and BCR/ABL antagonist.

Compositions of the invention are also used in combination with other active ingredients. For the treatment of Arenaviridae virus infections, preferably, the other active therapeutic agent is active against Arenaviridae virus infections, particularly Lassa virus and Junin virus infections. Non-limiting examples of these other active therapeutic agents are Ribavirin, Favipiravir (also known as T-705 or Avigan), T-705 monophosphate, T-705 diphosphate, T-705 triphosphate, ST-193, and mixtures thereof. RNA-dependent RNA polymerase (RDRP) modulators such as Remdesivir. The compounds and compositions of the present invention are also intended for use with general care provided patients with Arenaviridae viral infections, including parenteral fluids (including dextrose saline and Ringer's lactate) and nutrition, antibiotic (including Metronidazole and Cephalosporin antibiotics, such as Ceftriaxone and Cefuroxime) and/or antifungal prophylaxis, fever and pain medication, antiemetic (such as Metoclopramide) and/or antidiarrheal agents, vitamin and mineral supplements (including Vitamin C or/and K and zinc sulfate), anti-inflammatory agents (such as Ibuprofen), anti-inflammatory and immunosuppressant agents such as Dexamethasone; pain medications, and medications for other common diseases in the patient population, such anti-malarial agents (including Artemether and Artesunate-lumefantrine combination therapy), typhoid (including quinolone antibiotics, such as Ciprofloxacin, macrolide antibiotics, such as Azithromycin, cephalosporin antibiotics, such as Ceftriaxone, or aminopenicillins, such as Ampicillin), or shigellosis.

While the present invention has been described in terms of its specific embodiments, certain modifications and equivalents will be apparent to those skilled in the art and are intended to be included within the scope of the present invention.

We claim:

1. A compound having the structure of general formula (I)

Formula (I)

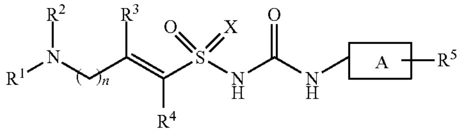

or a tautomeric form, stereoisomer, enantiomer, or a pharmaceutically acceptable salt thereof, and pharmaceutical compositions containing said compound wherein each of R1 and R2 at each occurrence independently selected from the group consisting of hydrogen, halogen, haloalkyl, cyano, and optionally substituted groups selected from (C1-C6)alkyl, (C1-C6)haloalkyl, (C2-C6)alkenyl, (C2-C6)alkynyl, (C1-C6)alkoxy, (C3-C7)cycloalkyl, (C1-C6)alkylSO2(C1-C6)alkyl, (C1-C6)alkylN(C1-C6)alkyl, (C1-C6)alkylN(C3-C7)cycloalkyl, aryl, heteroaryl, heterocyclyl, benzyl, tert-butyloxycarbonyl, thiol, mercaptoalkyl, SO2(C1-C6)alkyl, SO2(C3-C7)cycloalkyl, SO2-aryl, SO2-heterocyclyl, (C1-C6)thioalkyl, (C1-C6)thioalkoxy, (C1-C6)alkylSO2NH2, —CONH2, —CO(C1-C6)alkyl, —CO(C1-C6)haloalkyl, CO(O)(C1-C6)alkyl, —CO-aryl, —CO-heteroaryl, —CO-heterocyclyl, 4- to 7-membered heterocyclic ring, 7- to 14-membered bicyclic heterocyclic ring system, and bridged or spiro ring system having optionally one or more than one heteroatom; or, alternatively, R1, R2 and N together may form a saturated or partially saturated 3 to 8 membered heterocyclic ring system, 7- to 14-membered bicyclic heterocyclic ring system, bridged or spiro ring system having optionally one or more than one heteroatom; wherein each of R3 and R4 at each occurrence is selected from the group consisting of hydrogen, halogen, haloalkyl, cyano, nitro, amide, sulphonamide, acyl, hydroxyl, and optionally substituted groups selected from (C1-C6)alkyl, (C1-C6)haloalkyl, (C3-C6)cycloalkyl, (C1-C6)alkoxy, SO2(C1-C6)alkyl, thiol, mercapto alkyl benzyl, aryl, heteroaryl, and heterocyclyl; or, alternatively R3 and R4 may form a bond;

X is O, N—R6; wherein R6 at each occurrence independently is selected from the group consisting of hydrogen, hydroxyl, halogen, nitro, cyano, haloalkyl, and optionally substituted groups selected from (C1-C10) alkyl, (C1-C10)alkoxy, (C3-C10)cycloalkyl, (C2-C10) alkenyl, (C2-C10)alkynyl, SO2(C1-C6)alkyl, thiol, thioalkyl, thio-alkoxy, SO2(C1-C6)alkyl, SO(C1-C6) alkyl, benzyl, aryl, heteroaryl, and heterocyclyl; n, is independently selected from integer 0-3; wherein R5 at each occurrence independently is selected from the group consisting of hydrogen, halogen, haloalkyl, cyano, and optionally substituted groups selected from (C1-C6)alkyl, (C1-C6)alkoxy, (C2-C6)alkenyl, (C3-C7)cycloalkyl, benzyl, aryl, heteroaryl, heterocyclyl, thiol, thioalkyl, thio-alkoxy, SO2(C1-C6)alkyl, SO(C1-C6)alkyl, and bridged or spiro ring system having optionally one or more than one heteroatom;

'A' is selected from one of the following ring systems

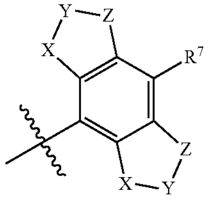

and

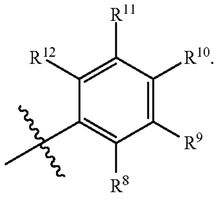

wherein X, Y, Z at each occurrence independently is selected from the group consisting of C, N, S, SO2, and O, which may be optionally substituted; and wherein each of R7, R8, R9, R10, R11 and R12 at each occurrence are independently selected from the group consisting of hydrogen, halogen, cyano, amide, sulphonamide, acyl, hydroxyl, and optionally substituted groups selected from (C1-C6)alkyl, (C1-C6)haloalkyl, (C3-C6)cycloalkyl, (C1-C6)alkoxy, benzyl, aryl, heteroaryl, and heterocyclyl; or, alternatively, each of R8 and R9, R9 and R10, R10 and R11 and R11 and R12 wherever possible, together may form a 4 to 7 membered saturated or partially saturated ring containing from 0-2 additional heteroatoms selected from the group consisting of N, O, and S(O)p; wherein p is 1-2.

2. The compound as claimed in claim 1, wherein R3 and R4 at each occurrence is independently selected from the group consisting of hydrogen, halogen, and an optionally substituted (C1-C6)alkyl group.

3. The compound as claimed in claim 1, wherein R5 at each occurrence is independently selected from the group consisting of hydrogen, halogen, and an optionally substituted (C1-C6)alkyl group.

4. The compound as claimed in claim 1, wherein R6 at each occurrence is independently selected from hydrogen and cyano.

5. The compound as claimed in claim 1, wherein each of R7, R8, R9, R10, R11 and R12 at each occurrence is independently selected from the group consisting of hydrogen, halogen, and optionally substituted groups selected from (C1-C6)alkyl and (C1-C6)haloalkyl.

6. The compound as claimed in claim 1, wherein when any of R1, R2, R3, R4, R5, R6, R7, R8, R9, R10, R11 and R12 are substituted, the substitutions are selected from hydrogen, hydroxy, cyano, halo, haloalkyl, haloalkyloxy, alkylthio, (C1-C6)alkyl, (C2-C6)alkenyl, (C2-C6)alkynyl, (C3-C10)cycloalkyl, C1-(C1-C6)alkoxy, aryl, heterocyclyl, heteroaryl, —COR11, —CSR11, C(O)OR11, C(O)—R11, —C(O)—NR11R12, —C(S)—NR11R12, —SO2R11 group, wherein each of, R11 and R12 is independently selected from hydrogen, and optionally substituted group selected from (C1-C6)alkyl, (C2-C6)alkenyl, (C2-C6)alkynyl, (C3-C7)cycloalkyl, aryl, heteroaryl, and heterocyclyl groups.

7. A compound as claimed in claim 1 selected from the group consisting of:

(E)-N-((1,2,3,5,6,7-hexahydro-s-indacen-4-yl)carbamoyl)-3-(isopropylamino)prop-1-ene-1-sulfonamide;
(E)-3-(dimethylamino)-N-((1,2,3,5,6,7-hexahydro-s-indacen-4-yl)carbamoyl) prop-1-ene-1-sulfonamide;
(E)-N-((1,2,3,5,6,7-hexahydro-s-indacen-4-yl)carbamoyl)-3-(methyl(propyl)amino)prop-1-ene-1-sulfonamide;
(E)-N-((1,2,3,5,6,7-hexahydro-s-indacen-4-yl)carbamoyl)-3-(propylamino)prop-1-ene-1-sulfonamide;
(E)-3-((cyclopropylmethyl)amino)-N-((1,2,3,5,6,7-hexahydro-s-indacen-4-yl)carbamoyl) prop-1-ene-1-sulfonamide;
(E)-3-((cyclopropylmethyl)(methyl)amino)-N-((1,2,3,5,6,7-hexahydro-s-indacen-4-yl)carbamoyl) prop-1-ene-1-sulfonamide;
(E)-3-(ethyl(methyl)amino)-N-((1,2,3,5,6,7-hexahydro-s-indacen-4-yl)carbamoyl) prop-1-ene-1-sulfonamide;
(E)-N-((1,2,3,5,6,7-hexahydro-s-indacen-4-yl)carbamoyl)-3-(N-methylmethylsulfonamido)prop-1-ene-1-sulfonamide;
(E)-N-(3-(N-((1,2,3,5,6,7-hexahydro-s-indacen-4-yl)carbamoyl)sulfamoyl) allyl)-N-methylcyclopropanesulfonamide;
(E)-N-(3-(N-((1,2,3,5,6,7-hexahydro-s-indacen-4-yl)carbamoyl)sulfamoyl) allyl)-N-methylcyclohexanesulfonamide;
(E)-N-(3-(N-((1,2,3,5,6,7-hexahydro-s-indacen-4-yl)carbamoyl)sulfamoyl) allyl)cyclohexanesulfonamide;
(E)-3-((cyclohexylmethyl)amino)-N-((1,2,3,5,6,7-hexahydro-s-indacen-4-yl)carbamoyl) prop-1-ene-1-sulfonamide;
(E)-3-((cyclohexylmethyl)(methyl)amino)-N-((1,2,3,5,6,7-hexahydro-s-indacen-4-yl)carbamoyl) prop-1-ene-1-sulfonamide;
(E)-N-(3-(N-((1,2,3,5,6,7-hexahydro-s-indacen-4-yl)carbamoyl)sulfamoyl) allyl)-N-methylcyclohexanecarboxamide;
(E)-N-(3-(N-((1,2,3,5,6,7-hexahydro-s-indacen-4-yl)carbamoyl)sulfamoyl) allyl)-N-methylacetamide;
(E)-N-(3-(N-((1,2,3,5,6,7-hexahydro-s-indacen-4-yl)carbamoyl)sulfamoyl) allyl)-N-methylcyclopropanecarboxamide;
(E)-N-((2,6-diisopropylphenyl)carbamoyl)-3-(dimethylamino)prop-1-ene-1-sulfonamide;
(E)-N-((2,6-diisopropyl-4-methylphenyl)carbamoyl)-3-(dimethylamino)prop-1-ene-1-sulfonamide;
(E)-3-(dimethylamino)-N-((4-fluoro-2,6-diisopropylphenyl)carbamoyl) prop-1-ene-1-sulfonamide;
(E)-N-((1,2,3,5,6,7-hexahydro-s-indacen-4-yl)carbamoyl)-3-(methyl(phenyl)amino)prop-1-ene-1-sulfonamide;
(E)-N-((1,2,3,5,6,7-hexahydro-s-indacen-4-yl)carbamoyl)-3-(phenylamino)prop-1-ene-1-sulfonamide;
(E)-N-((1,2,3,5,6,7-hexahydro-s-indacen-4-yl)carbamoyl)-3-(thiazol-2-ylamino)prop-1-ene-1-sulfonamide;
(E)-N-((1,2,3,5,6,7-hexahydro-s-indacen-4-yl)carbamoyl)-3-(methyl(thiazol-2-yl)amino)prop-1-ene-1-sulfonamide;
(E)-N'-cyano-3-(dimethylamino)-N-((1,2,3,5,6,7-hexahydro-s-indacen-4-yl)carbamoyl) prop-1-ene-1-sulfonimidamide;
(E)-N'-cyano-3-(ethyl(methyl)amino)-N-((1,2,3,5,6,7-hexahydro-s-indacen-4-yl)carbamoyl) prop-1-ene-1-sulfonimidamide;
(E)-N'-cyano-3-((cyclopropylmethyl)(methyl)amino)-N-((1,2,3,5,6,7-hexahydro-s-indacen-4-yl)carbamoyl) prop-1-ene-1-sulfonimidamide;
(E)-N'-cyano-3-((cyclopropylmethyl)amino)-N-((1,2,3,5,6,7-hexahydro-s-indacen-4-yl)carbamoyl) prop-1-ene-1-sulfonimidamide;
(E)-N'-cyano-3-(dimethylamino)-N-((4-fluoro-2,6-diisopropylphenyl)carbamoyl) prop-1-ene-1-sulfonimidamide;
(E)-3-((cyclopropylmethyl)amino)-N-((1,2,3,5,6,7-hexahydro-s-indacen-4-yl)carbamoyl) prop-1-ene-1-sulfonimidamide;
(E)-3-((cyclopropylmethyl)(methyl)amino)-N-((1,2,3,5,6,7-hexahydro-s-indacen-4-yl)carbamoyl) prop-1-ene-1-sulfonimidamide;
(E)-3-(dimethylamino)-N-((1,2,3,5,6,7-hexahydro-s-indacen-4-yl)carbamoyl) prop-1-ene-1-sulfonimidamide;
(E)-3-(dimethylamino)-N-((4-fluoro-2,6-diisopropylphenyl)carbamoyl) prop-1-ene-1-sulfonimidamide;
(E)-3-(dimethylamino)-N-((1,2,3,5,6,7-hexahydro-s-indacen-4-yl)carbamoyl)-N'-methylprop-1-ene-1-sulfonimidamide;
(E)-N'-cyano-N-((1,2,3,5,6,7-hexahydro-s-indacen-4-yl) carbamoyl)-3-(methyl(oxetan-3-yl)amino)prop-1-ene-1-sulfonimidamide;
(E)-N'-cyano-N-((1,2,3,5,6,7-hexahydro-s-indacen-4-yl) carbamoyl)-3-(oxetan-3-ylamino)prop-1-ene-1-sulfonimidamide;
(E)-N-((1,2,3,5,6,7-hexahydro-s-indacen-4-yl)carbamoyl)-3-(oxetan-3-ylamino)prop-1-ene-1-sulfonimidamide;
(E)-N-((1,2,3,5,6,7-hexahydro-s-indacen-4-yl)carbamoyl)-3-(oxetan-3-ylamino)prop-1-ene-1-sulfonamide
(E)-N-((1,2,3,5,6,7-hexahydro-s-indacen-4-yl)carbamoyl)-3-(5-methylhexahydropyrrolo[3,4-c]pyrrol-2 (1H)-yl) prop-1-ene-1-sulfonamide;
(E)-N-((1,2,3,5,6,7-hexahydro-s-indacen-4-yl)carbamoyl)-3-(hexahydropyrrolo[3,4-c]pyrrol-2 (1H)-yl) prop-1-ene-1-sulfonamide;
(E)-N-((1,2,3,5,6,7-hexahydro-s-indacen-4-yl)carbamoyl)-3-(5-(methylsulfonyl) hexahydropyrrolo[3,4-c] pyrrol-2 (1H)-yl) prop-1-ene-1-sulfonamide;

(E)-N-((1,2,3,5,6,7-hexahydro-s-indacen-4-yl)carbamoyl)-3-(hexahydropyrrolo[3,4-c]pyrrol-2 (1H)-yl) prop-1-ene-1-sulfonamide;

(E)-N-((1,2,3,5,6,7-hexahydro-s-indacen-4-yl)carbamoyl)-3-(tetrahydro-1H-furo[3,4-c]pyrrol-5 (3H)-yl) prop-1-ene-1-sulfonamide;

(E)-N-((1,2,3,5,6,7-hexahydro-s-indacen-4-yl)carbamoyl)-3-(3,4,5,6-tetrahydropyrrolo[3,4-c]pyrrol-2 (1H)-yl) prop-1-ene-1-sulfonamide; and (E)-N-((1,2,3,5,6,7-hexahydro-s-indacen-4-yl)carbamoyl)-3-(5-(methylsulfonyl)-3,4,5,6-tetrahydropyrrolo [3,4-c]pyrrol-2 (1H)-yl) prop-1-ene-1-sulfonamide or a pharmaceutically acceptable salt of any of the compounds above.

8. A pharmaceutical composition comprising a therapeutically effective amount of a compound of Formula (I) as claimed in claim 1 and optionally one or more pharmaceutically acceptable carriers, diluents or excipients.

9. The pharmaceutical composition as claimed in claim 8 in combination with one or more suitable pharmaceutically active agents selected from inhibitors of interleukin-1β; immune-suppressants; metabolic disorders drugs, glucocorticoids, non-steroidal anti-inflammatory drugs, COX-2 specific inhibitors, anti-inflammatory drugs, TNF-α binding proteins, interferon-13, interferon, interleukin-2, antihistamines, beta-agonists, BTK inhibitors, anticholinergics, anticancer agents or their suitable pharmaceutically acceptable salts, Non-Alcoholic Steato-Hepatitis (NASH) and fibrosis drugs, antibiotics, hormones, aromatase inhibitors, inhibitors of mitogen-activated protein kinase signaling, Syk inhibitors, mTOR inhibitors, BCR/ABL antagonists, Arenaviridae virus infections, Lassa virus infections, Junin virus infections, antibiotic and/or antifungal prophylaxis, fever and pain medication, antiemetic and/or antidiarrheal agents, vitamin and mineral supplements, anti-inflammatory agents, anti-inflammatory and immunosuppressant agents, pain medications, and medications for other common diseases in the patient population, anti-malarial agents and cephalosporin antibiotics.

10. A method of treating diseases medicated by the NLRP3 modulators as well as treatment of diseases or conditions in which interleukin 1β activity and interleukin-18 (IL-18) are implicated, comprising the step of administering to a patient in need thereof an effective amount of a compound of Formula (I) as claimed in claim 1 or its suitable pharmaceutical composition.

11. The method of claim 10, wherein each NLRP3 modulator has a pathophysiological function.

* * * * *